US009725499B2

(12) United States Patent
Conticello et al.

(10) Patent No.: US 9,725,499 B2
(45) Date of Patent: Aug. 8, 2017

(54) SELF-ASSEMBLING COLLAGEN-LIKE POLYPEPTIDE SEQUENCES FOR APPLICATIONS AND USES RELATED THERETO

(71) Applicant: EMORY UNIVERSITY, Atlanta, GA (US)

(72) Inventors: Vincent Paul Conticello, Decatur, GA (US); Tao Jiang, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/640,635

(22) Filed: Mar. 6, 2015

(65) Prior Publication Data

US 2015/0252096 A1    Sep. 10, 2015

Related U.S. Application Data

(60) Provisional application No. 61/949,334, filed on Mar. 7, 2014.

(51) Int. Cl.
*C07K 14/78* (2006.01)
*B32B 5/26* (2006.01)

(52) U.S. Cl.
CPC ........... *C07K 14/78* (2013.01); *B32B 5/26* (2013.01); *B32B 2307/73* (2013.01); *B32B 2535/00* (2013.01); *Y10T 428/31728* (2015.04)

(58) Field of Classification Search
CPC .................................................. C07K 14/78
See application file for complete search history.

(56) References Cited

U.S. PATENT DOCUMENTS 5,580,712 A * 12/1996 Keevert, Jr. ........... C07K 14/78
430/567
2009/0264626 A1   10/2009 Raines
2009/0299034 A1   12/2009 Cejas

OTHER PUBLICATIONS

Babu et al. "Enhanced Triple Helix Stability of Collagen Peptides with 4R-Aminoprolyl (Amp) Residues: Relative Roles of Electrostatic and Hydrogen Bonding Effects" J. Am. Chem. Soc., 2001; 123: 2079-2080.
Chattopadhyay "Collagen mimetic peptides for wound assessment and healing" ProQuest Dissertations and Theses; 2012.
Dehsorkhi et al. "Self-assembling amphiphilic peptides" J Pept Sci., 2014; 20(7): 453-467.
Egelman et al. "Structural Plasticity of Helical Nanotubes Based on Coiled-Coil Assemblies" Structure, 2015; 23: 280-289.
Fallas et al. "Rational Design of Single-Composition ABC Collagen Heterotrimers" J. Am. Chem. Soc., 2012; 134(3): 1430-1433.
Gauba et al. "Synthetic Collagen Heterotrimers: Structural Mimics of Wild-Type and Mutant Collagen Type I" J. Am. Chem. Soc., 2008; 130(23): 7509-7515.
Hamley et al. "Self-assembled arginine-coated peptide nanosheets in water" Chem Commun (Camb)., Mar. 4, 2013; 49(18): 1850-1852.
Jiang et al. "Structurally Homogeneous Nanosheets from Self-Assembly of a Collagen-Mimetic Peptide" Angewandte Chemie International Edition, 2014; 53: 8367-8371.
Jiang et al. "Structurally Defined Nanoscale Sheets from Self-Assembly of Collagen-Mimetic Peptides" J. Am. Chem. Soc., 2014; 136(11): 4300-4308.
Jiang et al. "Rational Design of Multilayer Collagen Nanosheets with Compositional and Structural Control" Journal of the American Chemical Society, 2015; 137(24): 7793-7802.
O'Leary et al. "Multi-hierarchical self-assembly of a collagen mimetic peptide from triple helix to nanofibre and hydrogel" Nature Chemistry, 2011; 3: 821-828.
O'Leary et al. "Positive and Negative Design Leads to Compositional Control in AAB Collagen Heterotrimers" J. Am. Chem. Soc., 2011; 133(14): 5432-5443.
Przybyla et al. "Hierarchical Assembly of Collagen Peptide Triple Helices into Curved Disks and Metal Ion-Promoted Hollow Spheres" J. Am. Chem. Soc., 2013: 135(9): 3418-3422.
Rele et al. "D-Periodic Collagen-Mimetic Microfibers" J. Am. Chem. Soc., 2007; 129(47): 14780-14787.
Russell et al. "Selective Assembly of a High Stability AAB Collagen Heterotrimer" J. Am. Chem. Soc., 2010; 132: 3242-3243.
Umashankara et al. "Two prolines with a difference: contrasting stereoelectronic effects of 4R/S-aminoproline on triplex stability in collagen peptides [Pro(X)-Pro(Y)-Gly]n" Chem. Commun., 2003; 2606-2607.
Xu et al. "Self-Assembly of Left- and Right-Handed Molecular Screws" J. Am. Chem. Soc., 2013; 135(50): 18762-18765.
Yu et al. "Collagen mimetic peptides: progress towards functional applications" Soft Matter, 2011; 7: 7927-7938.

* cited by examiner

*Primary Examiner* — Amber D Steele
(74) *Attorney, Agent, or Firm* — Emory Patent Group

(57) ABSTRACT

This disclosure relates to collagen like polypeptides, applications, and uses related thereto. In certain embodiments, the disclosure relates to collagen like polypeptides wherein hydroxy proline is substituted with amino proline and containing amino acids having side chains with carboxylic acids wherein the polypeptides are configured through electrostatic interactions of the amine and carboxylic acid groups to form solid structures. In certain embodiments, the disclosure contemplates modifications of these polypeptides in order to impart desirable properties to the solid structures.

20 Claims, 11 Drawing Sheets

(Pro-Yaa-Gly)$_4$–(Pro-Hyp-Gly)$_n$–(Xaa-Hyp-Gly)$_4$

CPII: Xaa = Glu;   Yaa = Arg;   n = 4
      Xaa = Asp;   Yaa = Lys;   n = 4
NSI:  Xaa = Glu;   Yaa = Amp;   n = 4
NSII: Xaa = Glu;   Yaa = Amp;   n = 7

(4R)-Hyp          (4R)-Amp

NSI: (Pro-Amp-Gly)₄–(Pro-Hyp-Gly)₄–(Glu-Hyp-Gly)₄
NSIII: (amp-Hyp-Gly)₄–(Pro-Hyp-Gly)₄–(Pro-Glu-Gly)₄
FIG. 6A
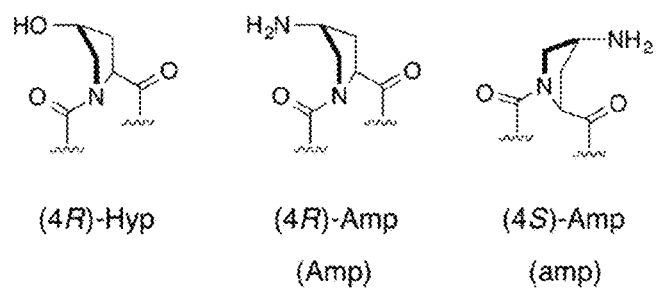
(4R)-Hyp     (4R)-Amp     (4S)-Amp
             (Amp)        (amp)
FIG. 6B
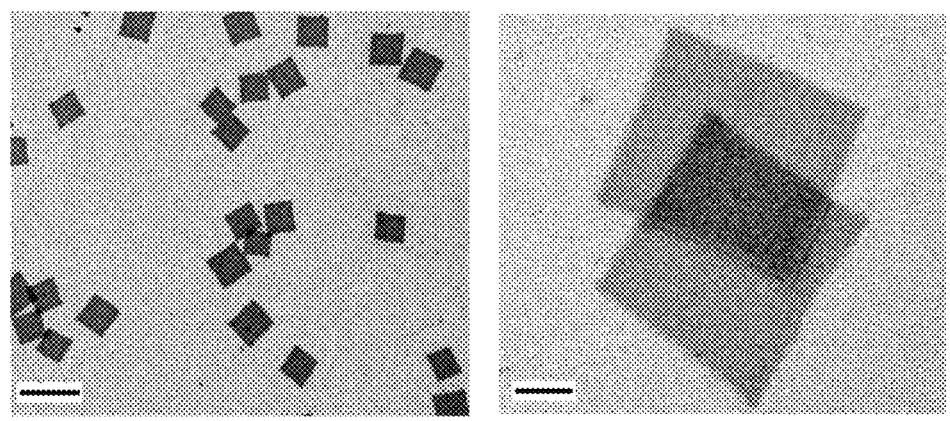
FIG. 7A     FIG. 7B

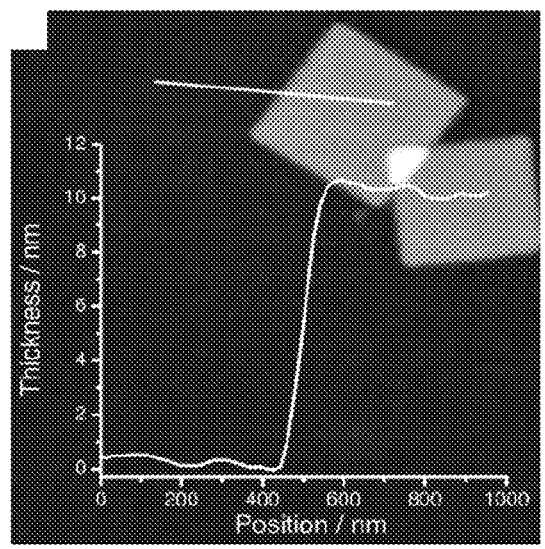
FIG. 7C.
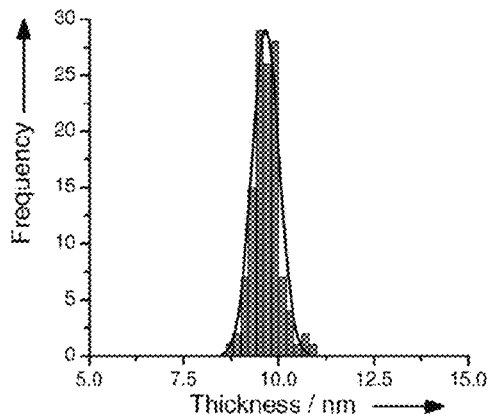
FIG. 7D
NS+ (Pro-Arg-Gly)$_7$-(Pro-Hyp-Gly)$_4$-(Glu-Hyp-Gly)$_4$
NS- (Pro-Arg-Gly)$_4$-(Pro-Hyp-Gly)$_4$-(Glu-Hyp-Gly)$_7$
FIG. 8A

SEQUENCE LISTING

<160> NUMBER OF SEQ ID NOS: 9

<210> SEQ ID NO 1
<211> LENGTH: 36
<212> TYPE: PRT
<213> ORGANISM: Artificial Sequence
<220> FEATURE:
<223> OTHER INFORMATION: Synthetic constructs
<220> FEATURE:
<221> NAME/KEY: MISC_FEATURE
<222> LOCATION: (1)..(1)
<223> OTHER INFORMATION: Where X is any amino acid
<220> FEATURE:
<221> NAME/KEY: MISC_FEATURE -continued

```
<222> LOCATION: (2)..(2)
<223> OTHER INFORMATION: Where X is any amino acid
<220> FEATURE:
<221> NAME/KEY: MISC_FEATURE
<222> LOCATION: (4)..(4)
<223> OTHER INFORMATION: Where X is any amino acid
<220> FEATURE:
<221> NAME/KEY: MISC_FEATURE
<222> LOCATION: (5)..(5)
<223> OTHER INFORMATION: Where X is any amino acid
<220> FEATURE:
<221> NAME/KEY: MISC_FEATURE
<222> LOCATION: (7)..(7)
<223> OTHER INFORMATION: Where X is any amino acid
<220> FEATURE:
<221> NAME/KEY: MISC_FEATURE
<222> LOCATION: (8)..(8)
<223> OTHER INFORMATION: Where X is any amino acid
<220> FEATURE:
<221> NAME/KEY: MISC_FEATURE
<222> LOCATION: (10)..(10)
<223> OTHER INFORMATION: Where X is any amino acid
<220> FEATURE:
<221> NAME/KEY: MISC_FEATURE
<222> LOCATION: (11)..(11)
<223> OTHER INFORMATION: Where X is any amino acid
<220> FEATURE:
<221> NAME/KEY: MISC_FEATURE
<222> LOCATION: (13)..(13)
<223> OTHER INFORMATION: Where X is any amino acid
<220> FEATURE:
<221> NAME/KEY: MISC_FEATURE
<222> LOCATION: (14)..(14)
<223> OTHER INFORMATION: Where X is any amino acid
<220> FEATURE:
<221> NAME/KEY: MISC_FEATURE
<222> LOCATION: (16)..(16)
<223> OTHER INFORMATION: Where X is any amino acid
<220> FEATURE:
<221> NAME/KEY: MISC_FEATURE
<222> LOCATION: (17)..(17)
<223> OTHER INFORMATION: Where X is any amino acid
<220> FEATURE:
<221> NAME/KEY: MISC_FEATURE
<222> LOCATION: (19)..(19)
<223> OTHER INFORMATION: Where X is any amino acid
<220> FEATURE:
<221> NAME/KEY: MISC_FEATURE
<222> LOCATION: (20)..(20)
<223> OTHER INFORMATION: Where X is any amino acid
<220> FEATURE:
<221> NAME/KEY: MISC_FEATURE
<222> LOCATION: (22)..(22)
<223> OTHER INFORMATION: Where X is any amino acid
<220> FEATURE:
<221> NAME/KEY: MISC_FEATURE
<222> LOCATION: (23)..(23)
<223> OTHER INFORMATION: Where X is any amino acid
<220> FEATURE:
<221> NAME/KEY: MISC_FEATURE
<222> LOCATION: (25)..(25)
<223> OTHER INFORMATION: Where X is any amino acid
<220> FEATURE:
<221> NAME/KEY: MISC_FEATURE
<222> LOCATION: (26)..(26)
<223> OTHER INFORMATION: Where X is any amino acid
<220> FEATURE:
<221> NAME/KEY: MISC_FEATURE
<222> LOCATION: (28)..(28)
<223> OTHER INFORMATION: Where X is any amino acid
<220> FEATURE:
<221> NAME/KEY: MISC_FEATURE
<222> LOCATION: (29)..(29)
<223> OTHER INFORMATION: Where X is any amino acid
<220> FEATURE:
<221> NAME/KEY: MISC_FEATURE
<222> LOCATION: (31)..(31)
<223> OTHER INFORMATION: Where X is any amino acid
<220> FEATURE:
```

```
<221> NAME/KEY: MISC_FEATURE
<222> LOCATION: (32)..(32)
<223> OTHER INFORMATION: Where X is any amino acid
<220> FEATURE:
<221> NAME/KEY: MISC_FEATURE
<222> LOCATION: (34)..(34)
<223> OTHER INFORMATION: Where X is any amino acid
<220> FEATURE:
<221> NAME/KEY: MISC_FEATURE
<222> LOCATION: (35)..(35)
<223> OTHER INFORMATION: Where X is any amino acid

<400> SEQUENCE: 1

Xaa Xaa Gly Xaa Xaa Gly Xaa Xaa Gly Xaa Xaa Gly Xaa Xaa Gly Xaa
1               5                   10                  15

Xaa Gly Xaa Xaa Gly Xaa Xaa Gly Xaa Xaa Gly Xaa Xaa Gly Xaa Xaa
            20                  25                  30

Gly Xaa Xaa Gly
        35

<210> SEQ ID NO 2
<211> LENGTH: 36
<212> TYPE: PRT
<213> ORGANISM: Artificial Sequence
<220> FEATURE:
<223> OTHER INFORMATION: Synthetic constructs
<220> FEATURE:
<221> NAME/KEY: MISC_FEATURE
<222> LOCATION: (14)..(14)
<223> OTHER INFORMATION: Where X is hydroxyproline
<220> FEATURE:
<221> NAME/KEY: MISC_FEATURE
<222> LOCATION: (17)..(17)
<223> OTHER INFORMATION: Where X is hydroxyproline
<220> FEATURE:
<221> NAME/KEY: MISC_FEATURE
<222> LOCATION: (20)..(20)
<223> OTHER INFORMATION: Where X is hydroxyproline
<220> FEATURE:
<221> NAME/KEY: MISC_FEATURE
<222> LOCATION: (23)..(23)
<223> OTHER INFORMATION: Where X is hydroxyproline
<220> FEATURE:
<221> NAME/KEY: MISC_FEATURE
<222> LOCATION: (26)..(26)
<223> OTHER INFORMATION: Where X is hydroxyproline
<220> FEATURE:
<221> NAME/KEY: MISC_FEATURE
<222> LOCATION: (29)..(29)
<223> OTHER INFORMATION: Where X is hydroxyproline
<220> FEATURE:
<221> NAME/KEY: MISC_FEATURE
<222> LOCATION: (32)..(32)
<223> OTHER INFORMATION: Where X is hydroxyproline
<220> FEATURE:
<221> NAME/KEY: MISC_FEATURE
<222> LOCATION: (35)..(35)
<223> OTHER INFORMATION: Where y is hydroxyproline

<400> SEQUENCE: 2

Pro Lys Gly Pro Lys Gly Pro Lys Gly Pro Lys Gly Pro Xaa Gly Pro
1               5                   10                  15

Xaa Gly Pro Xaa Gly Pro Xaa Gly Asp Xaa Gly Asp Xaa Gly Asp Xaa
            20                  25                  30

Gly Asp Xaa Gly
        35

<210> SEQ ID NO 3
<211> LENGTH: 36
<212> TYPE: PRT
<213> ORGANISM: Artificial Sequence
```

```
<220> FEATURE:
<223> OTHER INFORMATION: Synthetic constructs
<220> FEATURE:
<221> NAME/KEY: MISC_FEATURE
<222> LOCATION: (14)..(14)
<223> OTHER INFORMATION: Where X is hydroxyproline
<220> FEATURE:
<221> NAME/KEY: MISC_FEATURE
<222> LOCATION: (17)..(17)
<223> OTHER INFORMATION: Where X is hydroxyproline
<220> FEATURE:
<221> NAME/KEY: MISC_FEATURE
<222> LOCATION: (20)..(20)
<223> OTHER INFORMATION: Where X is hydroxyproline
<220> FEATURE:
<221> NAME/KEY: MISC_FEATURE
<222> LOCATION: (23)..(23)
<223> OTHER INFORMATION: Where X is hydroxyproline
<220> FEATURE:
<221> NAME/KEY: MISC_FEATURE
<222> LOCATION: (26)..(26)
<223> OTHER INFORMATION: Where X is hydroxyproline
<220> FEATURE:
<221> NAME/KEY: MISC_FEATURE
<222> LOCATION: (29)..(29)
<223> OTHER INFORMATION: Where X is hydroxyproline
<220> FEATURE:
<221> NAME/KEY: MISC_FEATURE
<222> LOCATION: (32)..(32)
<223> OTHER INFORMATION: Where X is hydroxyproline
<220> FEATURE:
<221> NAME/KEY: MISC_FEATURE
<222> LOCATION: (35)..(35)
<223> OTHER INFORMATION: Where Y is hydroxyproline

<400> SEQUENCE: 3

Pro Arg Gly Pro Arg Gly Pro Arg Gly Pro Arg Gly Pro Xaa Gly Pro
1               5                   10                  15

Xaa Gly Pro Xaa Gly Pro Xaa Gly Glu Xaa Gly Glu Xaa Gly Glu Xaa
            20                  25                  30

Gly Glu Xaa Gly
        35

<210> SEQ ID NO 4
<211> LENGTH: 36
<212> TYPE: PRT
<213> ORGANISM: Artificial Sequence
<220> FEATURE:
<223> OTHER INFORMATION: Synthetic constructs
<220> FEATURE:
<221> NAME/KEY: MISC_FEATURE
<222> LOCATION: (2)..(2)
<223> OTHER INFORMATION: Where X is (2S,4R)-4-aminoproline
<220> FEATURE:
<221> NAME/KEY: MISC_FEATURE
<222> LOCATION: (5)..(5)
<223> OTHER INFORMATION: Where X is (2S,4R)-4-aminoproline
<220> FEATURE:
<221> NAME/KEY: MISC_FEATURE
<222> LOCATION: (8)..(8)
<223> OTHER INFORMATION: Where X is (2S,4R)-4-aminoproline
<220> FEATURE:
<221> NAME/KEY: MISC_FEATURE
<222> LOCATION: (11)..(11)
<223> OTHER INFORMATION: Where X is (2S,4R)-4-aminoproline
<220> FEATURE:
<221> NAME/KEY: MISC_FEATURE
<222> LOCATION: (14)..(14)
<223> OTHER INFORMATION: Where X is hydroxyproline
<220> FEATURE:
<221> NAME/KEY: MISC_FEATURE
<222> LOCATION: (17)..(17)
<223> OTHER INFORMATION: Where X is hydroxyproline
<220> FEATURE:
<221> NAME/KEY: MISC_FEATURE
```

```
<222> LOCATION: (20)..(20)
<223> OTHER INFORMATION: Where X is hydroxyproline
<220> FEATURE:
<221> NAME/KEY: MISC_FEATURE
<222> LOCATION: (23)..(23)
<223> OTHER INFORMATION: Where X is hydroxyproline
<220> FEATURE:
<221> NAME/KEY: MISC_FEATURE
<222> LOCATION: (26)..(26)
<223> OTHER INFORMATION: Where X is hydroxyproline
<220> FEATURE:
<221> NAME/KEY: MISC_FEATURE
<222> LOCATION: (29)..(29)
<223> OTHER INFORMATION: Where X is hydroxyproline
<220> FEATURE:
<221> NAME/KEY: MISC_FEATURE
<222> LOCATION: (32)..(32)
<223> OTHER INFORMATION: Where X is hydroxyproline
<220> FEATURE:
<221> NAME/KEY: MISC_FEATURE
<222> LOCATION: (35)..(35)
<223> OTHER INFORMATION: Where X is hydroxyproline

<400> SEQUENCE: 4

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Glu Xaa Gly Glu Xaa Gly Glu Xaa
            20                  25                  30

Gly Glu Xaa Gly
        35

<210> SEQ ID NO 5
<211> LENGTH: 45
<212> TYPE: PRT
<213> ORGANISM: Artificial Sequence
<220> FEATURE:
<223> OTHER INFORMATION: Synthetic constructs
<220> FEATURE:
<221> NAME/KEY: MISC_FEATURE
<222> LOCATION: (2)..(2)
<223> OTHER INFORMATION: Where X is (2S,4S)-4-aminoproline
<220> FEATURE:
<221> NAME/KEY: MISC_FEATURE
<222> LOCATION: (5)..(5)
<223> OTHER INFORMATION: Where X is (2S,4S)-4-aminoproline
<220> FEATURE:
<221> NAME/KEY: MISC_FEATURE
<222> LOCATION: (8)..(8)
<223> OTHER INFORMATION: Where X is (2S,4S)-4-aminoproline
<220> FEATURE:
<221> NAME/KEY: MISC_FEATURE
<222> LOCATION: (11)..(11)
<223> OTHER INFORMATION: Where X is (2S,4S)-4-aminoproline
<220> FEATURE:
<221> NAME/KEY: MISC_FEATURE
<222> LOCATION: (14)..(14)
<223> OTHER INFORMATION: Where X is hydroxyproline
<220> FEATURE:
<221> NAME/KEY: MISC_FEATURE
<222> LOCATION: (17)..(17)
<223> OTHER INFORMATION: Where X is hydroxyproline
<220> FEATURE:
<221> NAME/KEY: MISC_FEATURE
<222> LOCATION: (20)..(20)
<223> OTHER INFORMATION: Where X is hydroxyproline
<220> FEATURE:
<221> NAME/KEY: MISC_FEATURE
<222> LOCATION: (23)..(23)
<223> OTHER INFORMATION: Where X is hydroxyproline
<220> FEATURE:
<221> NAME/KEY: MISC_FEATURE
<222> LOCATION: (26)..(26)
<223> OTHER INFORMATION: Where X is hydroxyproline
<220> FEATURE:
<221> NAME/KEY: MISC_FEATURE
```

```
<222> LOCATION: (29)..(29)
<223> OTHER INFORMATION: Where X is hydroxyproline
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: MISC_FEATURE
<222> LOCATION: (35)..(35)
<223> OTHER INFORMATION: Where X is hydroxyproline
<220> FEATURE:
<221> NAME/KEY: MISC_FEATURE
<222> LOCATION: (38)..(38)
<223> OTHER INFORMATION: Where X is hydroxyproline
<220> FEATURE:
<221> NAME/KEY: MISC_FEATURE
<222> LOCATION: (41)..(41)
<223> OTHER INFORMATION: Where X is hydroxyproline
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: MISC_FEATURE
<222> LOCATION: (45)..(45)
<223> OTHER INFORMATION: Where X is hydroxyproline

<400> SEQUENCE: 5

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Glu Xaa Gly Glu Xaa Gly Glu Xaa
            20                  25                  30

Gly Glu Xaa Gly Glu Xaa Gly Glu Xaa Gly Glu Xaa Gly
        35                  40                  45

<210> SEQ ID NO 6
<211> LENGTH: 36
<212> TYPE: PRT
<213> ORGANISM: Artificial Sequence
<220> FEATURE:
<223> OTHER INFORMATION: Synthetic constructs
<220> FEATURE:
<221> NAME/KEY: MISC_FEATURE
<222> LOCATION: (1)..(1)
<223> OTHER INFORMATION: where X is (2S,4S)-4-aminoproline
<220> FEATURE:
<221> NAME/KEY: MISC_FEATURE
<222> LOCATION: (2)..(2)
<223> OTHER INFORMATION: where X is hydroxyproline
<220> FEATURE:
<221> NAME/KEY: MISC_FEATURE
<222> LOCATION: (4)..(4)
<223> OTHER INFORMATION: where X is (2S,4S)-4-aminoproline
<220> FEATURE:
<221> NAME/KEY: MISC_FEATURE
<222> LOCATION: (5)..(5)
<223> OTHER INFORMATION: where X is hydroxyproline
<220> FEATURE:
<221> NAME/KEY: MISC_FEATURE
<222> LOCATION: (7)..(7)
<223> OTHER INFORMATION: where X is (2S,4S)-4-aminoproline
<220> FEATURE:
<221> NAME/KEY: MISC_FEATURE
<222> LOCATION: (8)..(8)
<223> OTHER INFORMATION: where X is hydroxyproline
<220> FEATURE:
<221> NAME/KEY: MISC_FEATURE
<222> LOCATION: (10)..(10)
<223> OTHER INFORMATION: where X is (2S,4S)-4-aminoproline
<220> FEATURE:
<221> NAME/KEY: MISC_FEATURE
<222> LOCATION: (11)..(11)
<223> OTHER INFORMATION: where X is hydroxyproline
<220> FEATURE:
<221> NAME/KEY: MISC_FEATURE
```

```
<222> LOCATION: (14)..(14)
<223> OTHER INFORMATION: where X is hydroxyproline
<220> FEATURE:
<221> NAME/KEY: MISC_FEATURE
<222> LOCATION: (17)..(17)
<223> OTHER INFORMATION: where X is hydroxyproline
<220> FEATURE:
<221> NAME/KEY: MISC_FEATURE
<222> LOCATION: (20)..(20)
<223> OTHER INFORMATION: where X is hydroxyproline
<220> FEATURE:
<221> NAME/KEY: MISC_FEATURE
<222> LOCATION: (23)..(23)
<223> OTHER INFORMATION: where X is hydroxyproline

<400> SEQUENCE: 6

Xaa Xaa Gly Xaa Xaa Gly Xaa Xaa Gly Xaa Xaa Gly Pro Xaa Gly Pro
1               5                   10                  15

Xaa Gly Pro Xaa Gly Pro Xaa Gly Pro Glu Gly Pro Glu Gly Pro Glu
            20                  25                  30

Gly Pro Glu Gly
        35

<210> SEQ ID NO 7
<211> LENGTH: 45
<212> TYPE: PRT
<213> ORGANISM: Artificial Sequence
<220> FEATURE:
<223> OTHER INFORMATION: Synthetic constructs
<220> FEATURE:
<221> NAME/KEY: MISC_FEATURE
<222> LOCATION: (23)..(23)
<223> OTHER INFORMATION: where X is hydroxyproline
<220> FEATURE:
<221> NAME/KEY: MISC_FEATURE
<222> LOCATION: (26)..(26)
<223> OTHER INFORMATION: where X is hydroxyproline
<220> FEATURE:
<221> NAME/KEY: MISC_FEATURE
<222> LOCATION: (29)..(29)
<223> OTHER INFORMATION: where X is hydroxyproline
<220> FEATURE:
<221> NAME/KEY: MISC_FEATURE
<222> LOCATION: (32)..(32)
<223> OTHER INFORMATION: where X is hydroxyproline
<220> FEATURE:
<221> NAME/KEY: MISC_FEATURE
<222> LOCATION: (35)..(35)
<223> OTHER INFORMATION: where X is hydroxyproline
<220> FEATURE:
<221> NAME/KEY: MISC_FEATURE
<222> LOCATION: (38)..(38)
<223> OTHER INFORMATION: where X is hydroxyproline
<220> FEATURE:
<221> NAME/KEY: MISC_FEATURE
<222> LOCATION: (41)..(41)
<223> OTHER INFORMATION: where X is hydroxyproline
<220> FEATURE:
<221> NAME/KEY: MISC_FEATURE
<222> LOCATION: (44)..(44)
<223> OTHER INFORMATION: where X is hydroxyproline

<400> SEQUENCE: 7

Pro Arg Gly Pro Arg Gly Pro Arg Gly Pro Arg Gly Pro Arg Gly Pro
1               5                   10                  15

Arg Gly Pro Arg Gly Pro Xaa Gly Pro Xaa Gly Pro Xaa Gly Pro Xaa
            20                  25                  30

Gly Glu Xaa Gly Glu Xaa Gly Glu Xaa Gly Glu Xaa Gly
        35                  40                  45

<210> SEQ ID NO 8
```

-continued

```
<211> LENGTH: 46
<212> TYPE: PRT
<213> ORGANISM: Artificial Sequence
<220> FEATURE:
<223> OTHER INFORMATION: Synthetic constructs
<220> FEATURE:
<221> NAME/KEY: MISC_FEATURE
<222> LOCATION: (15)..(15)
<223> OTHER INFORMATION: Where  X is hydroxyproline
<220> FEATURE:
<221> NAME/KEY: MISC_FEATURE
<222> LOCATION: (18)..(18)
<223> OTHER INFORMATION: Where  X is hydroxyproline
<220> FEATURE:
<221> NAME/KEY: MISC_FEATURE
<222> LOCATION: (21)..(21)
<223> OTHER INFORMATION: Where  X is hydroxyproline
<220> FEATURE:
<221> NAME/KEY: MISC_FEATURE
<222> LOCATION: (24)..(24)
<223> OTHER INFORMATION: Where  X is hydroxyproline
<220> FEATURE:
<221> NAME/KEY: MISC_FEATURE
<222> LOCATION: (27)..(27)
<223> OTHER INFORMATION: Where  X is hydroxyproline
<220> FEATURE:
<221> NAME/KEY: MISC_FEATURE
<222> LOCATION: (30)..(30)
<223> OTHER INFORMATION: Where  X is hydroxyproline
<220> FEATURE:
<221> NAME/KEY: MISC_FEATURE
<222> LOCATION: (33)..(33)
<223> OTHER INFORMATION: Where  X is hydroxyproline
<220> FEATURE:
<221> NAME/KEY: MISC_FEATURE
<222> LOCATION: (36)..(36)
<223> OTHER INFORMATION: Where  X is hydroxyproline
<220> FEATURE:
<221> NAME/KEY: MISC_FEATURE
<222> LOCATION: (39)..(39)
<223> OTHER INFORMATION: Where  X is hydroxyproline
<220> FEATURE:
<221> NAME/KEY: MISC_FEATURE
<222> LOCATION: (42)..(42)
<223> OTHER INFORMATION: Where  X is hydroxyproline
<220> FEATURE:
<221> NAME/KEY: MISC_FEATURE
<222> LOCATION: (45)..(45)
<223> OTHER INFORMATION: Where  X is hydroxyproline

<400> SEQUENCE: 8

Pro Arg Gly Pro Arg Gly Pro Arg Gly Pro Arg Gly Pro Pro Xaa Gly
1               5                   10                  15

Pro Xaa Gly Pro Xaa Gly Pro Xaa Gly Glu Xaa Gly Glu Xaa Gly Glu
                20                  25                  30

Xaa Gly Glu Xaa Gly Glu Xaa Gly Glu Xaa Gly Glu Xaa Gly
            35                  40                  45

<210> SEQ ID NO 9
<211> LENGTH: 45
<212> TYPE: PRT
<213> ORGANISM: Artificial Sequence
<220> FEATURE:
<223> OTHER INFORMATION: Synthetic constructs
<220> FEATURE:
<221> NAME/KEY: MISC_FEATURE
<222> LOCATION: (2)..(2)
<223> OTHER INFORMATION: Where X is hydroxyproline
<220> FEATURE:
<221> NAME/KEY: MISC_FEATURE
<222> LOCATION: (5)..(5)
<223> OTHER INFORMATION: Where X is hydroxyproline
<220> FEATURE:
<221> NAME/KEY: MISC_FEATURE
<222> LOCATION: (8)..(8)
```

```
<223> OTHER INFORMATION: Where X is hydroxyproline
<220> FEATURE:
<221> NAME/KEY: MISC_FEATURE
<222> LOCATION: (11)..(11)
<223> OTHER INFORMATION: Where X is hydroxyproline
<220> FEATURE:
<221> NAME/KEY: MISC_FEATURE
<222> LOCATION: (14)..(14)
<223> OTHER INFORMATION: Where X is hydroxyproline
<220> FEATURE:
<221> NAME/KEY: MISC_FEATURE
<222> LOCATION: (17)..(17)
<223> OTHER INFORMATION: Where X is hydroxyproline
<220> FEATURE:
<221> NAME/KEY: MISC_FEATURE
<222> LOCATION: (20)..(20)
<223> OTHER INFORMATION: Where X is hydroxyproline
<220> FEATURE:
<221> NAME/KEY: MISC_FEATURE
<222> LOCATION: (23)..(23)
<223> OTHER INFORMATION: Where X is hydroxyproline
<220> FEATURE:
<221> NAME/KEY: MISC_FEATURE
<222> LOCATION: (26)..(26)
<223> OTHER INFORMATION: Where X is hydroxyproline
<220> FEATURE:
<221> NAME/KEY: MISC_FEATURE
<222> LOCATION: (29)..(29)
<223> OTHER INFORMATION: Where X is hydroxyproline
<220> FEATURE:
<221> NAME/KEY: MISC_FEATURE
<222> LOCATION: (32)..(32)
<223> OTHER INFORMATION: Where X is hydroxyproline
<220> FEATURE:
<221> NAME/KEY: MISC_FEATURE
<222> LOCATION: (35)..(35)
<223> OTHER INFORMATION: Where X is hydroxyproline
<220> FEATURE:
<221> NAME/KEY: MISC_FEATURE
<222> LOCATION: (38)..(38)
<223> OTHER INFORMATION: Where X is hydroxyproline
<220> FEATURE:
<221> NAME/KEY: MISC_FEATURE
<222> LOCATION: (41)..(41)
<223> OTHER INFORMATION: Where X is hydroxyproline
<220> FEATURE:
<221> NAME/KEY: MISC_FEATURE
<222> LOCATION: (44)..(44)
<223> OTHER INFORMATION: Where X is hydroxyproline

<400> SEQUENCE: 9

Asp Xaa Gly Asp Xaa Gly Asp Xaa Gly Asp Xaa Gly Asp Xaa Gly Asp
1               5                   10                  15

Xaa Gly Asp Xaa Gly Pro Xaa Gly Pro Xaa Gly Pro Xaa Gly Pro Xaa
            20                  25                  30

Gly Glu Xaa Gly Glu Xaa Gly Glu Xaa Gly Glu Xaa Gly
        35                  40                  45
```

SELF-ASSEMBLING COLLAGEN-LIKE POLYPEPTIDE SEQUENCES FOR APPLICATIONS AND USES RELATED THERETO

CROSS REFERENCE TO RELATED APPLICATIONS

This application claims priority to U.S. Provisional Application No. 61/949,334 filed Mar. 7, 2014, which application is hereby incorporated by reference in its entirety.

STATEMENT REGARDING FEDERALLY FUNDED RESEARCH

This invention was made with government support under Grant CHE1012620 awarded by the National Science Foundation. The government has certain rights in the invention.

BACKGROUND

Collagen is a ubiquitous material living organisms use to create structure through the self-assembly of fibrillogenic proteins. It is desirable to design improved materials with biological, chemical, and mechanical properties that mimic collage as it is typically biocompatible. The triple-helical domain of native collagen comprises a recurrence of a tripeptide repeat sequence Xaa-Yaa-Gly. The amino acids in the Xaa and Yaa positions vary; however from a statistical standpoint, Proline (Pro) and (4R)-hydroxyproline (Hyp), respectively, most frequently occupy the these positions. The assembly of synthetic collagen triple helices has been reported. See, e.g., Rele et al. JACS, 2007, 129, 14780-14787; Gauba et al., JACS, 2008, 130(23):7509-7515; Russell et al., JACS, 2010, 132 (10):3242-3243; O'Leary et al., Nature Chemistry, 2011, 3, 821-828, O'Leary et al., JACS, 2011, 133 (14), 5432-5443; and Fallas et al., JACS, 2012, 134 (3):1430-1433.

The self-assembly of synthetic collagen into two or three dimensional structures desirable for fabricating artificial medical devices or implantable material has been challenging. Thus, there is a need to identify improved materials. Przybyla et al. report hierarchical assembly of collagen peptide triple helices into curved disks and metal ion-promoted hollow spheres. JACS, 2013, 135 (9):3418-3422. Xu et al., report self-Assembly of left- and right-handed molecular screws. JACS, 2013, 135 (50):18762-18765.

Babu & Ganesh report collagen peptides with 4R-aminoprolyl (Amp) residues. JACS, 2001, 123(9):2079-80. See also Umashankara et al., Chem Commun (Camb), 2003, (20):2606-7.

Arginine-coated peptides are reported to self-assemble to nanosheets in water. Hamley et al., Chem Commun (Camb), 2013, 49(18):1850-2.

References cited herein are not an admission of prior art.

SUMMARY

This disclosure relates to collagen like polypeptides, applications, and uses related thereto. In certain embodiments, the disclosure relates to collagen like polypeptides wherein hydroxy proline is substituted with amino proline and containing amino acids having side chains with carboxylic acids wherein the polypeptides are configured through electrostatic interactions of the amine and carboxylic acid groups to form solid structures. In certain embodiments, the disclosure contemplates modifications of these polypeptides in order to impart desirable properties to the solid structures.

In certain embodiments, the disclosure relates to polypeptides comprising a) an first terminal segment comprising a three amino acid repeat starting with two amino acids, wherein one of the two amino acids is proline substituted with an amino group, and ending with a glycine; b) a middle segment comprising a three amino acid repeat starting with two amino acids, wherein one of the two amino acids comprises a side chain with an hydroxy group, and ending with a glycine; c) a second terminal segment comprising a three amino acid repeat starting with two amino acids, wherein one of the two amino acids comprises side chain with a carboxylic acid group, and ending with a glycine.

In certain embodiments, the amino proline or proline substituted with an amino group is (2S,4S)-4-aminoproline.

In certain embodiments, the disclosure relates a purified polypeptide of SEQ ID NO: 3, 4, 5, 6, 7, 8, 9 or functioning variants thereof e.g., with one or two amino acid substitutions, additions, deletions; or variants thereof with three or more amino acid substitutions, additions, deletions.

In certain embodiments, the first terminal segment comprises a three amino acid repeat starting with two amino acids, wherein one of the two amino acids is a hydrophobic amino acid, wherein one of the two amino acids is proline substituted with an amino group, and ending with a glycine.

In certain embodiments, the middle segment comprises a three amino acid repeat starting with two amino acids, wherein one of the two amino acids is a hydrophobic amino acid, wherein one of the two amino acids comprises a side chain with a hydroxy group, and ending with a glycine.

In certain embodiments, the second terminal segment comprises a three amino acid repeat starting with two amino acids, wherein one of the two amino acids comprises side chain with a carboxylic acid group, wherein one of the two amino acids comprises a side chain with a hydroxy group, and ending with a glycine.

In certain embodiments, the hydrophobic amino acid is proline.

In certain embodiments, one of the two amino acids comprising a side chain with a hydroxy group is proline substituted with a hydroxy group.

In certain embodiments, the first terminal segment is the N-terminal segment and the second terminal segment is the C-terminal segment. In certain embodiments, the first terminal segment is the N-terminal segment and the N-terminal amino acid is (2S,4S)-4-aminoproline.

In certain embodiments, the disclosure relates to compositions comprising a polypeptide comprising the sequence $(X^1-Y^1-Gly)_m-(X^2-Y^2-Gly)_n-(X^3-Y^3-Gly)_p$ (SEQ ID NO:1, when m, n, and p are 4) wherein, $X^1$ is any amino acid, $Y^1$ is any amino acid, m is three or more,
provided that proline is the most common $X^1$,
provided that proline substituted with an amino group is the most common $Y^1$;

$X^2$ is any amino acid, $Y^2$ is any amino acid, n is three or more,
provided that proline is the most common $X^2$,
provided that proline substituted with an hydroxy group is the most common $Y^2$;

$X^3$ is any amino acid, $Y^3$ is any amino acid, p is three or more,
provided that an amino acid comprises side chain with a carboxylic acid group is the most common $X^3$, provided that proline substituted with an hydroxy group is the most common $Y^3$.

In certain embodiments, $X^1$ is proline and $Y^1$ is aminoproline.

In certain embodiments, $X^2$ is proline and $Y^2$ is hydoxyproline.

In certain embodiments, $X^3$ is Glu or Asp and $Y^3$ is hydroxyproline.

In certain embodiments, the disclosure relates to compositions comprising a polypeptide comprising the sequence $(X^1-Y^1\text{-Gly})_m\text{-}(X^2-Y^2\text{-Gly})_n\text{-}(X^3-Y^3\text{-Gly})_p$ (SEQ ID NO:1)
wherein,
$X^1$ is any amino acid, $Y^1$ is any amino acid, m is three or more,
provided that that proline substituted with an amino group is the most common $X^1$,
provided that proline substituted with an hydroxy group is the most common $Y^1$.
$X^2$ is any amino acid, $Y^2$ is any amino acid, n is three or more,
provided that proline is the most common $X^2$,
provided that proline substituted with an hydroxy group is the most common $Y^2$.
$X^3$ is any amino acid, $Y^3$ is any amino acid, p is three or more,
provided that proline is the most common $X^3$,
provided that an amino acid comprises side chain with a carboxylic acid group is the most common $Y^3$.

In certain embodiments, $X^1$ is (2S,4S)-4-aminoproline.

In certain embodiments, $X^1$ is (2S,4S)-4-aminoproline and $Y^1$ is hydroxyproline.

In certain embodiments, $X^2$ is proline and $Y^2$ is hydoxyproline.

In certain embodiments, $X^3$ is proline and $Y^3$ is Glu or Asp.

In certain embodiments, m is 2 to 1000, or 3 to 100, or 4 to 20, or 4 to 10, n is 2 to 1000, or 3 to 100, or 4 to 20, or 4 to 10, p is m is 2 to 1000, or 3 to 100, or 4 to 20, or 4 to 10.

In certain embodiments, the disclosure relates to a polypeptide comprising (amp-Hyp-Gly)$_m$(Pro-Hyp-Gly)$_n$(Pro-$Y^3$-Gly)$_p$ (SEQ ID NO: 6) wherein m, n, p are 4, or wherein m is 2 to 1000, or 3 to 100, or 4 to 20, or 4 to 10, n is 2 to 1000, or 3 to 100, or 4 to 20, or 4 to 10, p is m is 2 to 1000, or 3 to 100, or 4 to 20, or 4 to 10, amp is (2S,4S)-4-aminoproline, and $Y^3$ is Glu or Asp.

In certain embodiments, n is greater than m and p, or n is less than m and p, or n is different than m and p, or n, m, and p are the same, or n is m plus 1-4 or m minus 1-4, or n is p plus 1-4 or p minus 1-4, or m is n plus 1-4 or n minus 1-4, or m is p plus 1-4 or p minus 1-4, or p is n plus 1-4 or n minus 1-4, or p is m plus 1-4 or m minus 1-4, or combinations thereof.

In certain embodiments, the polypeptide is terminally linked to a polyethylene glycol, biotin, hydrocarbon chain, steroid, therapeutic agent, antibody, antibody epitope, protein, ligand, receptor, oligonucleotide, chelating agent, or combinations thereof.

In certain embodiments, the disclosure relates to two-dimensional material comprising a polypeptide disclosed herein. In certain embodiments the two-dimensional material is a sheet between 8 and 12 nanometers thick.

In certain embodiments, the two-dimensional material disclosed herein has two or more polypeptides that are not identical. In certain embodiments, at least one polypeptide is terminally linked to a polyethylene glycol, biotin, hydrocarbon chain, steroid, therapeutic agent, antibody, antibody epitope, protein, ligand, receptor, oligonucleotide, chelating agent, or combinations thereof.

In certain embodiments, the disclosure relates to three-dimensional materials comprising a two-dimensional material disclosed herein. In certain embodiments, the three-dimensional material is glass, ceramic, silicon wafer, fluoropolymer, metal, metal oxide, semi-conducting material, transparent polymer, opaque polymer, medical device, implantable device or combinations thereof.

In certain embodiments, the disclosure relates to methods of making a two- or three-dimensional material comprising mixing a polypeptide disclosed herein in a liquid under conditions such that a solid comprising the polypeptide forms.

In certain embodiments, the disclosure relates to a material comprising 1) a first layer comprised of first polypeptide fibers comprising a) an first terminal segment comprising a three amino acid repeat starting with two amino acids, wherein one of the two amino acids is an amino acid comprising a side chain substituted with an amino group, and ending with a glycine; b) a middle segment comprising a three amino acid repeat starting with two amino acids, wherein one of the two amino acids comprises a side chain with an hydroxy group, and ending with a glycine; c) a second terminal segment comprising a three amino acid repeat starting with two amino acids, wherein one of the two amino acids comprises side chain with a carboxylic acid group, and ending with a glycine; and 2) a second layer comprising second polypeptide fibers comprising a) an first terminal segment comprising a three amino acid repeat starting with two amino acids, wherein one of the two amino acids is an amino acid comprising a side chain substituted with an amino group, and ending with a glycine; b) a middle segment comprising a three amino acid repeat starting with two amino acids, wherein one of the two amino acids comprises a side chain with an hydroxy group, and ending with a glycine; c) a second terminal segment comprising a three amino acid repeat starting with two amino acids, wherein one of the two amino acids comprises side chain with a carboxylic acid group, and ending with a glycine.

In certain embodiments, the first and second polypeptide fibers are configured perpendicular/vertical to the horizontal plane of the layers/sheet.

In certain embodiments, the first terminal segment of the first polypeptide fibers has a different length or one or more extra three amino acid repeats than the first terminal segment of the second polypeptide fiber and optionally the first polypeptide fibers and the second polypeptide fibers are of the same length.

In certain embodiments, the second terminal segment of the first polypeptide fibers has a different length or one or more extra three amino acid repeats than the second terminal segment of the second polypeptide fibers and optionally the first polypeptide fibers and the second polypeptide fibers are of the same length.

In certain embodiments, the disclosure relates to compositions comprising a first and second polypeptide comprising the sequence
$(X^1-Y^1\text{-Gly})_m\text{-}(X^2-Y^2\text{-Gly})_n\text{-}(X^3-Y^3\text{-Gly})_p$ (SEQ ID NO:1)
wherein,
$X^1$ is any amino acid, $Y^1$ is any amino acid, m is three or more,
provided that proline is the most common $X^1$, provided that an amino acid comprising a side chain with an amino group is the most common $Y^1$;

$X^2$ is any amino acid, $Y^2$ is any amino acid, n is three or more, provided that proline is the most common $X^2$, provided that proline substituted with an hydroxy group is the most common $Y^2$.

$X^3$ is any amino acid, $Y^3$ is any amino acid, p is three or more, provided that an amino acid comprising a side chain with a carboxylic acid group is the most common $X^3$, provided that proline substituted with an hydroxy group is the most common $Y^3$;

wherein m and p are selected from:

wherein in the first polypeptide sequence, m is larger than p, wherein in the second polypeptide sequence, p is larger than m, wherein in the first polypeptide sequence, p is larger than m, wherein in the second polypeptide sequence, m is larger than p, or combinations thereof In certain embodiments, the disclosure relates to compositions comprising a first and second polypeptide comprising the sequence $(X^1-Y^1-Gly)_m-(X^2-Y^2-Gly)_n-(X^3-Y^3-Gly)_p$ (SEQ ID NO:1)

wherein, $X^1$ is any amino acid, $Y^1$ is any amino acid, m is three or more, provided that an amino acid comprising a side chain with an amino group is the most common $X^1$, provided that is hydroxyproline the most common $Y^1$;

$X^2$ is any amino acid, $Y^2$ is any amino acid, n is three or more, provided that proline is the most common $X^2$, provided that proline substituted with an hydroxy group is the most common $Y^2$;

$X^3$ is any amino acid, $Y^3$ is any amino acid, p is three or more, provided that proline is the most common $X^3$, provided that an amino acid comprising a side chain with a carboxylic acid group is the most common $Y^3$;

wherein m and p are selected from:

wherein in the first polypeptide sequence, m is larger than p, wherein in the second polypeptide sequence, p is larger than m;

wherein in the first polypeptide sequence, p is larger than m, wherein in the second polypeptide sequence, m is larger than p, or combinations thereof.

In certain embodiments, m of the first polypeptide sequence is the same as the p of the second polypeptide sequence.

In certain embodiments, p of the first polypeptide sequence is the same as the m of the second polypeptide sequence.

In certain embodiments, the first polypeptide sequence is the same length or number of amino acids as the second polypeptide sequence.

BRIEF DESCRIPTION OF THE FIGURES

FIG. 6A shows the amino acid sequences of peptides NSI and NSIII $(amp-Hyp-Gly)_m(Pro-Hyp-Gly)_n(Pro-Glu-Gly)_p$, (SEQ ID NO: 6) wherein m, n, and p are 4, wherein amp is (2S,4S)-4-aminoproline.

FIG. 6B illustrates the structures and preferred ring pucker conformers of imino acid derivatives as shown in FIG. 6A.

FIG. 7A shows a TEM image of NSIII nanosheets at low magnification (scale bar=1 μm).

FIG. 7B shows a TEM image of NSIII nanosheets at high magnification (scale bar=150 nm).

FIG. 7C shows a representative AFM image and height profile of a single-layer nanosheets of NSIII (scale bar=300 nm).

FIG. 7D shows an AFM height histogram for single layer sheets of NSIII.

FIG. 8A shows NS+ (Pro-Arg-Gly)$_m$(Pro-Hyp-Gly)$_n$(Glu-Hyp-Gly)$_p$ (SEQ ID NO: 7) wherein m is 7, n is 4, and p is 4, and NS− (SEQ ID NO: 8) wherein m is 4, n is 4 and p is 7.

FIG. 9A shows data using atomic force microscope (AFM) to estimate the thickness of nanosheets from NS+ and NSI− under dry conditions.

FIG. 9B shows data using atomic force microscope (AFM) indicating that with the concentration ratio of NS−/NS+ less than two, layered structures appeared as small sheets staying on surfaces of large base nanosheets.

DETAILED DESCRIPTION

Figure 1A:
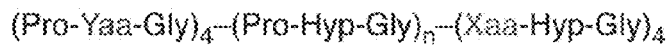
FIG. 1A illustrates certain embodiment of the disclosure. Amino acid sequences of peptides $(Pro-Yaa-Gly)_4(Pro-Hyp-Gly)_a(Xaa-Hyp-Gly)_4$. (SEQ ID NO: 2) wherein Xaa is Asp, n is 4, and Yaa is Lys. CPII (SEQ ID NO: 3) wherein Xaa is Glu, n is 4, and Yaa is Arg. NSI (SEQ ID NO: 4) wherein Xaa is Glu, n is 4, and Yaa is Amp. NSII (SEQ ID NO: 5) wherein Xaa is Glu, n is 7, and Yaa is Amp.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

Collagen Mimetic Peptides

Synthetic peptide sequences were forward engineered to self-assemble into structurally defined two-dimensional assemblies. The fibrillogenic peptide CPII was re-designed to introduce charge complementarity between triple helices in order to promote lateral assembly into layered structures. Biophysical measurements were conducted in solution and the solid-state on assemblies derived from the resultant peptides, NSI and NSII, over multiple length-scales of structural hierarchy. The accumulated data suggest that the underlying structure of these nanosheets can be understood in terms of the layered packing of collagen triple helices. Moreover, the chemical functionality displayed at the surface of the nanosheet enabled further elaboration of these structures through surface-localized chemical interactions.

The NSI and NSII nanosheets display a very high degree of internal order over large 2D length scales without recourse to introduction of non-native structural interactions. Moreover, the nanosheet thickness can be controlled through the peptide length and terminal functionality. The presence of functionalized capping groups provides the opportunity to control the surface chemistry to promote specific interaction with exogenous substrates that have been complementarily functionalized. The collagen triple helix represents a flexible experimental platform for creation of extended self-assembled 2D structures through structurally informed encoding of electrostatic interactions.

Sequence-encoded electrostatic interactions were employed to enforce alignment of a designed collagen mimetic peptide, CPII, into uniaxially oriented fibrils. See JACS, 2007, 129, 14780-14787. The design of peptide CPII comprised a symmetric sequence of three blocks of four triads, in which the triad sequence within each block encompassed different electrostatic properties. This block architecture was designed to promote a staggered alignment of peptides within a triple helical conformation in order to drive fibrillization through charge complementation. The CPII peptide self-assembles into fibrils that mimicked the banded, D periodic ultrastructure of native collagen fibers. However, the desired structural alignment was difficult to control under the extensive range of experimental conditions that were investigated for this peptide system.

Hartgerink and co-workers, based on an extensive structural analysis of electrostatic interactions within collagen-mimetic peptides, designed a derivative of CPII in which conservative substitutions of Asp for Glu and Lys for Arg were incorporated into the peptide sequence (FIG. 1A). See Gauba et al., JACS, 2008, 130(23):7509-7515. This second generation peptide underwent multi-hierarchical self-assembly under a wide range of experimental conditions to afford collagen-based hydrogels composed of laterally associated peptide fibrils. See O'Leary et al., Nature Chemistry, 2011, 3, 821-828.

Figure 1B:
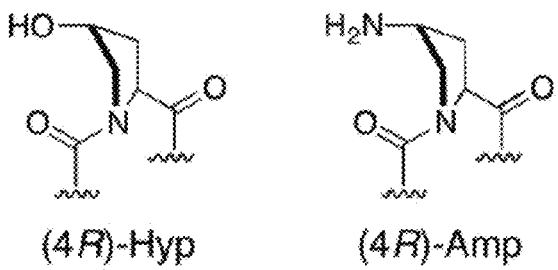
FIG. 1B illustrates structures and preferred ring pucker conformers of imino acid derivatives (Amp).

While fibrillar morphologies have been the predominant species observed thus far from self-assembly of CPII-like peptides, two-dimensional assemblies are not necessarily precluded based on the initial sequence design. Buffered aqueous solutions of CPII at near-neutral pH produced irregular sheet-like structures. Two sequence variants of the CPII peptide, NSI and NSII, were designed in order to bias self-assembly toward formation of two-dimensional layered assemblies through incorporation of structural features to promote selective interaction between helical bundles. The positively charged arginine residues in the first four triads of CPII were replaced with the non-canonical imino acid, (2S,4R)-4-aminoproline (Amp) (FIG. 1B). The stereo-electronic properties of Amp residue mirror those of the canonical (2S,4R)-4-hydroxyproline (Hyp) residue, in that the pyrrolidine ring adopts a C-4 exo ring pucker conformation.

The sequence of NSI is a structural analogue of the parent peptide CPII, while the sequence of NSII differs in that the central block of canonical (Pro-Hyp-Gly) triads was lengthened to seven repeats. Peptide NSII no longer mimics the symmetric triblock architecture of CPII. NSII in a staggered assembly does not assemble into one-dimensional fibrils.

Staking Peptide Nanosheets

In certain embodiments, the disclosure contemplates materials with three-directional sheet stacking preferences. In aqueous solutions, peptide sheets bearing the same charges were believed to remain monolayer in the presence of electrostatic repulsion between sheet surfaces. Treating peptide sheets with ones of opposite charges would generate the multi-layer structures. Through the "layer-by-layer adsorption", electrostatic attractions are used as driving force for multi-component system build-up. Ordered sheet stacking or growth is thought to be hindered by the long distance for electrostatic interactions that result in sheet adsorption at suboptimal angles. Thus, adding stud-like structures on peptide sheet surfaces was studied for improved engagement of these "studs" between surfaces in order to help organize sheet stacking in a more ordered manner.

EXAMPLES

Peptide Synthesis of NSI and NSII

Peptides NSI and NSII were prepared as the uncapped derivatives using microwave-assisted synthesis on a CEM Liberty solid-phase peptide synthesis instrument using an Fmoc-Gly-PEG-PS resin. Standard Fmoc protection chemistry was employed with coupling cycles based on HBTU/DIEA-mediated activation protocols and base-induced deprotection (20% piperidine in DMF with 0.1 M HOBt) of the Fmoc group. Peptides were purified via RP-HPLC on a C18 column with a gradient of water-acetonitrile with 0.1% trifluoroacetic acid. The target fractions were collected and lyophilized. The mass and purity were analyzed by matrix assisted laser desorption/ionization (MALDI) mass spectrometry and analytical HPLC. Peptides were dialyzed against deionized water thoroughly to remove residual trifluoroacetate (MWCO=2,000 Da). The resulting peptides were re-lyophilized, and stored at −20° C. before use. Peptides were dissolved in MOPS buffer (20 mM, pH 7.0). Solution concentrations were determined from the measured mass of the respective peptides. Samples were thermally annealed at 75° C. for 45 min, and gradually cooled to ambient temperature. Peptide NSII* was synthesized, purified, and assembled using an identical procedure with the exception that the N-terminus was capped with biotin-dPEG$_4$, using in situ activation of the corresponding free acid. The presence of biotin-dPEG4 capping group was confirmed using mass spectrometric analysis.

Circular Dichroism Spectra of Peptides NSI and NSII

CD spectra were recorded on a Jasco J-810 CD spectropolarimeter in 0.10 mm quartz cells in MOPS buffer (20 mM, pH 7.0). Spectra were recorded from 300 to 190 nm at a scanning rate of 100 nm/min and a resolution of 0.5 nm. CD melting experiments were performed in the temperature range from 5° C. to 80° C. at a heating rate of 1° C./min. The intensity of the CD signal at 224 nm was monitored as a function of temperature. Melting temperatures were obtained from the first derivative of the melting curves.

Figure 2A:
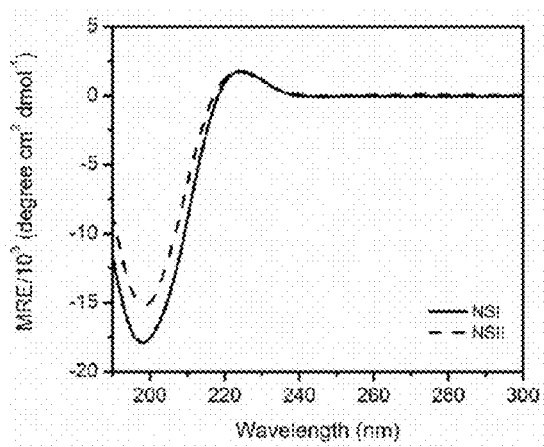
FIG. 2A shows circular dichroism spectra of peptides NSI (2 mg/mL) and NSII (2.5 mg/mL) in 20 mM MOPS buffer, pH 7.0.
Figure 2B:
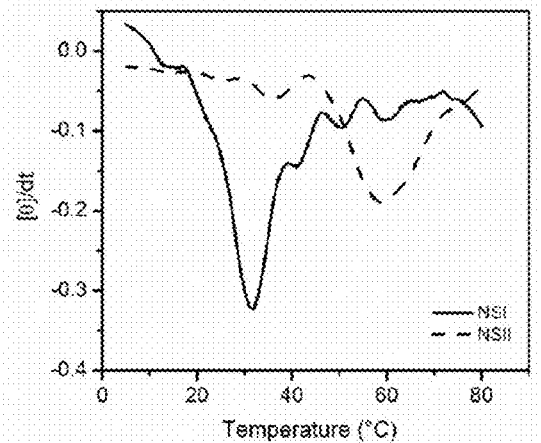
FIG. 2B shows a first derivative of the CD signal at 224 nm as a function of temperature. The Tm is estimated from the minimum in the first derivative curve as in FIG. 2A.

Circular dichroism (CD) spectropolarimetry of solutions of NSI (2 mg/mL) and NSII (2.5 mg/mL) in MOPS buffer displayed a characteristic collagen triple helical conformation, consisting of a positive maximum at 224 nm and a negative minimum at 198 nm (FIG. 2A). The RPN values, i.e., the ratio of intensities of the positive CD signal at 224 nm to the negative CD signal at 198 nm, were 0.10 and 0.11 for the solutions of NSI and NSII, respectively. An RPN value of ≥0.10 is consistent with a stable triple helical structure. Thermal denaturation studies were performed on solutions of the corresponding peptides, which afforded melting transitions (Tm) of 32° C. and 60° C. for NSI and NSII, respectively (FIG. 2B). The presence of three additional triads of (Pro-Hyp-Gly) in the central block of NSII increased the thermal stability of the triple helical conformation vis-à-vis that of NSI. The Tm values observed for solutions of NSI and NSII were significantly below the values expected for collagen-mimetic peptides containing an identical number of canonical (Pro-Hyp-Gly) triads. These data suggest that the aminoproline and glutamic acid residues within the NSI and NSII peptides thermodynamically destabilize the triple helical conformation. Ganesh et al., reported that Amp could be substituted in place of hydroxyproline (Hyp) in a collagen peptide consisting of six triad repeats (Pro-Amp-Gly). The corresponding peptide adopted a triple helical structure that was stable at both acidic and basic pH to a greater degree than a peptide of identical length based on the canonical triad repeat sequence (Pro-Hyp-Gly). However, these comparisons were drawn from CD spectropolarimetry of the corresponding peptides that was performed in the presence of 100 mM NaCl, which effectively screened the charge repulsion between Amp residues.

Figure 2C:
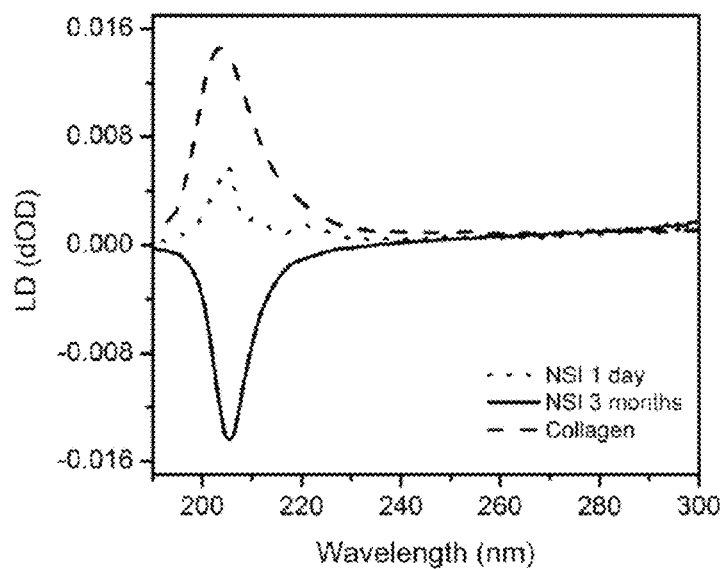
FIG. 2C shows flow linear dichroism spectra of nascent (0.5 mg/mL) and assembled (0.5 mg/mL) solutions of NSI in 20 mM MOPS buffer, pH 7.0 under a Couette flow of 2000 r.p.m. The flow LD spectrum of fibrillar type I collagen from rat-tail (0.4 mg/mL) in phosphate buffer solution (100 mM, pH 7.4) was employed under identical conditions as a standard of comparison.

Flow linear dichroism spectra were acquired under shear alignment for solutions of NSI as a function of incubation time to interrogate for the formation of assemblies (FIG. 2C). The sign and magnitude of the absorbances in flow linear dichroism can be correlated with the direction of polarization of the amide bond chromophores, which can be directly related to the orientation of self-assembled species in the flow field. Net orientation occurs for anisotropic self-assembled structures that persist under Couette flow.

Solutions of freshly dissolved NSI displayed a weak positive absorbance at a position coincident with that expected for collagen fibrils. However, incubation of the NSI solutions for a period of weeks at 4° C. resulted in a significant change in the flow LD spectrum. The amide bond absorbance displayed a polarization that was opposite to that of the initially prepared NSI specimen as well as that of fibrillar Type I collagen. The intensity of the signal for the mature NSI assemblies also increased significantly in comparison to the initial sample, approaching that of the fibrillar collagen preparation. The flow LD data support the formation of extended assemblies of NSI, in which the collagen triple helices are oriented in the flow field such that the long axis of the triple helix is perpendicular to the direction of flow. This arrangement would be consistent with assemblies consisting of layers of perpendicularly oriented collagen triple helices. In contrast, a flow LD signal was not observed for the more thermodynamically stable NSII, which did not preclude the formation of assemblies.

Transmission Electron Microscopy of NSI and NSII Assemblies

TEM specimens were prepared from aqueous solutions of NSI (2 mg/mL), NSII (2.5 mg/mL), or NSII* (10 mg/mL) in MOPS buffer (20 mM, pH 7.0). The samples were deposited onto 200 mesh carbon coated copper grids from Electron Microscopy Sciences (Hatfield, Pa.). After a 2 min incubation period, excess liquid was wicked away and the specimens were stained with an aqueous solution of uranyl acetate (1%). Excess stain was wicked away after incubation on the grid for 30 s. The sample grids were dried under vacuum and stored in a desiccator. TEM measurements were acquired on a Hitachi H-7500 transmission electron microscope at an accelerating voltage of 75 kV. For cationic gold nanoparticle staining experiments, both the solution of nanoparticles and NSII sheets were diluted 20 times with distilled, deionized $H_2O$. An aliquot (4 μL) of the diluted cationic gold solution was added to a solution (4 μL) of the diluted NSII sheets in situ, The mixture was incubated at ambient temperature for 20 min. Excess liquid was wicked away, and the specimens were then stained with uranyl acetate (1%) for 30 s. Excess stain solution was wicked away. Sample grids were dried in vacuum desiccator before TEM investigation.

Streptavidin-tagged gold nanoparticles were diluted 10-20 times with MOPS buffer (20 mM, pH 7.0). An aliquot (4-20 μL) of the diluted streptavidin-gold solution was added to 4 μL of NSII* sheets (10 mg/mL) in situ, and was incubated at ambient temperature for 20 min. Excess liquid was wicked away and the sample was washed three times for 5 min to remove the non-specifically bound streptavidin-gold solution. The specimens were then stained with uranyl acetate (1%) for 30 seconds. Excess stain solution was wicked away. Sample grids were dried in vacuum desiccator before TEM investigation.

The flow LD data suggested that solutions of NSI, and, by association, NSII, could self-assemble into supramolecular structures in solution. The formation of the assemblies was confirmed through correlative analysis with transmission electron microscopy (TEM) and atomic force microcopy (AFM). The self-assembly of NSI and NSII peptides in solution was monitored over time. The rate of formation of the assemblies was observed to depend on the concentration and molar mass of the peptide and ranged from weeks to hours. Dilute solutions of NSI (2 mg/mL in 20 mM MOPS, pH 7.0) assembled over a period of weeks, while more concentrated solutions (4 mg/mL) formed assemblies over a period of days. In contrast, solutions of NSII (2.5 mg/mL in 20 mM MOPS, pH 7.0) assembled over a period of hours.

Figure 3A:
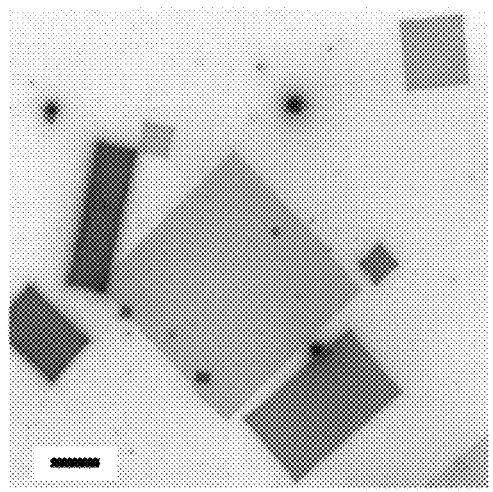
FIG. 3A shows a TEM image of NSI nanosheets indicating the polydisperse distribution of lateral size and thickness (scale bar=1 μm).
Figure 3B:
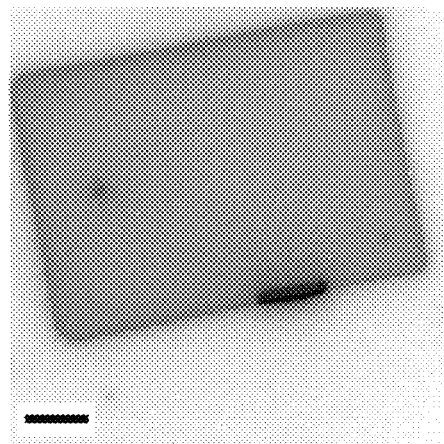
FIG. 3B shows a TEM image of an individual NSI nanosheet. (scale bar=1 μm)
Figure 3C:
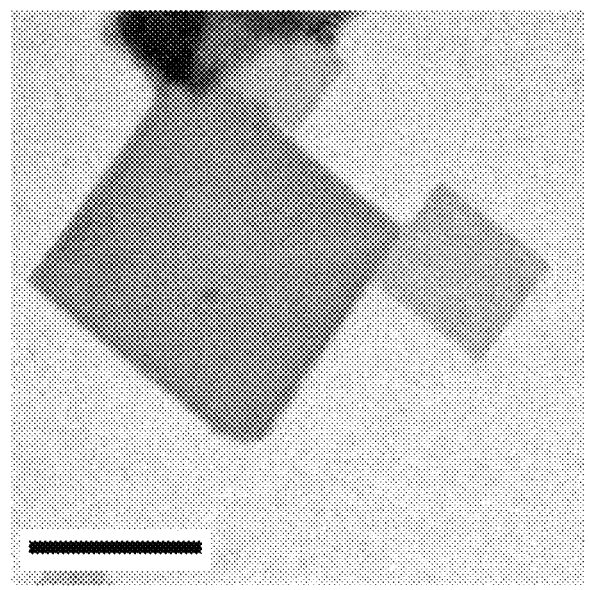
FIG. 3C shows a TEM image of representative nanosheets of NSII (scale bar=500 nm).

TEM of NSI and NSII assemblies were consistent with the presence of two-dimensional nano-scale sheets as the only observable self-assembled structures (FIG. 3A-C). Most commonly, the sheets occurred as fully formed tetragonal assemblies with cleanly defined edges in both lateral dimensions. On occasion, sheets were observed in stages of incomplete growth, in which well-defined terraces could be detected. Typically, the nanosheets displayed a wide dispersion in lateral dimensions; this polymorphism may be attributable to slow nucleation kinetics for sheet formation. This effect was more pronounced for sheets derived from NSI in comparison to NSII. In the former case, polymorphism could be detected not only in the plane of the sheet, but also in the direction normal to the plane. In the TEM images of NSI sheets, this dispersion in height was manifested in terms of differences in the electron contrast among the assemblies (FIG. 3A).

Figure 3D:
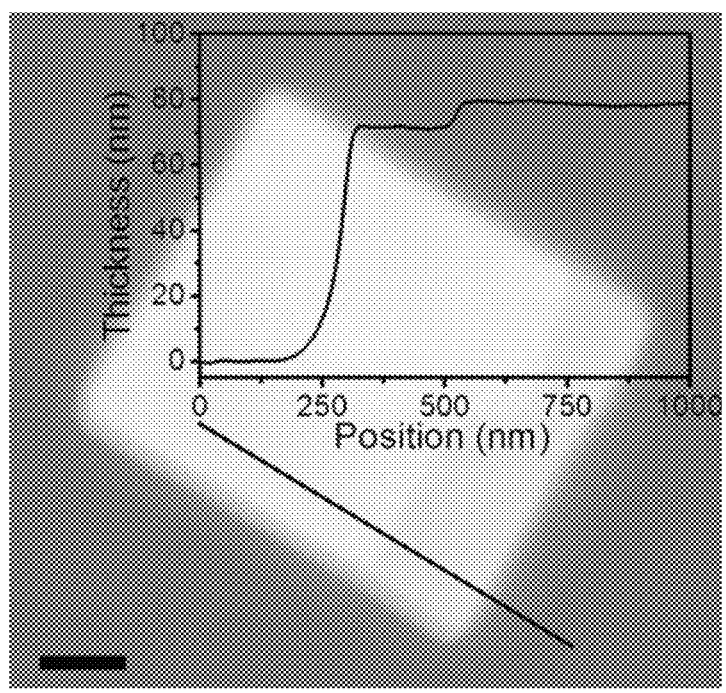
FIG. 3D shows a AFM image and height profile (inset) of a multi-layer nanosheet of NSI (scale bar=200 nm).
Figure 3E:
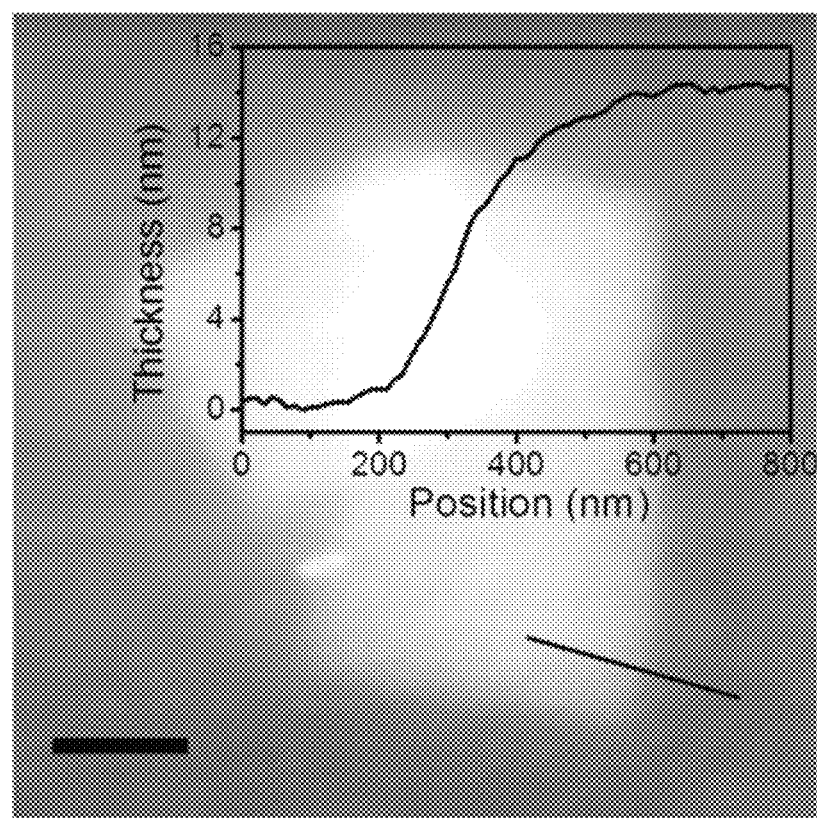
FIG. 3E shows a representative AFM image and height profile (inset) of a single-layer nanosheet of NSII (scale bar=200 nm).
Figure 3F:
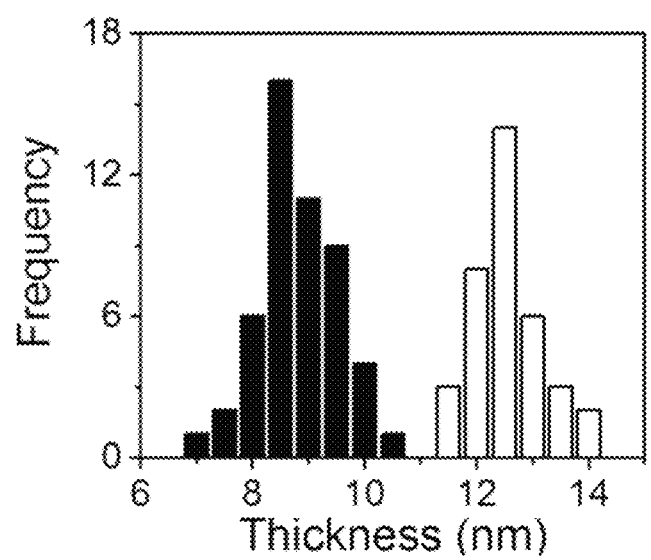
FIG. 3F shows a AFM height histogram for single-layer sheets of NSI (black) and NSII (white).

AFM analysis was employed to interrogate the height of the assemblies, which was observed to depend on the concentration and molar mass of the peptides (FIG. 3D-F). Solutions of NSI incubated for long periods under dilute conditions (2 mg/mL) afforded much thicker nanosheets, with heights up to circa 250 nm. More concentrated solutions of NSI (4 mg/mL) and solutions of NSII (2.5 mg/mL) resulted in thinner sheets. Nanosheets of NSII were typically only one or two layers in thickness (FIG. 3E). This observation may explain the absence of a flow LD signal for NSII, as the sheets may not be significantly robust to withstand the shear forces necessary for alignment. For the thicker sheets of NSI, AFM provided evidence for multiple stacked layers of collagen peptides, as terraces could be observed on the surface of the sheets that corresponded to growth of new layers (FIG. 3D). AFM measurements provided values of 8.8±0.8 nm and 12.3±0.7 nm for the heights of single-layer sheets of NSI and NSII, respectively (FIG. 3F). The calculated thickness for a layer comprising vertically oriented triple helices of NSI and NSII should be 10.3 nm and 12.9 nm, respectively (# residues×0.286 nm rise/residue). These data suggest that the nanosheets are composed of stacked layers of collagen triple helices. The difference in layer height between nanosheets derived from NSI and NSII could be attributed to the respective differences in peptide length projected onto a collagen triple helix.

Morphology of the NSI and NSII Nanosheets

Figure 4A:
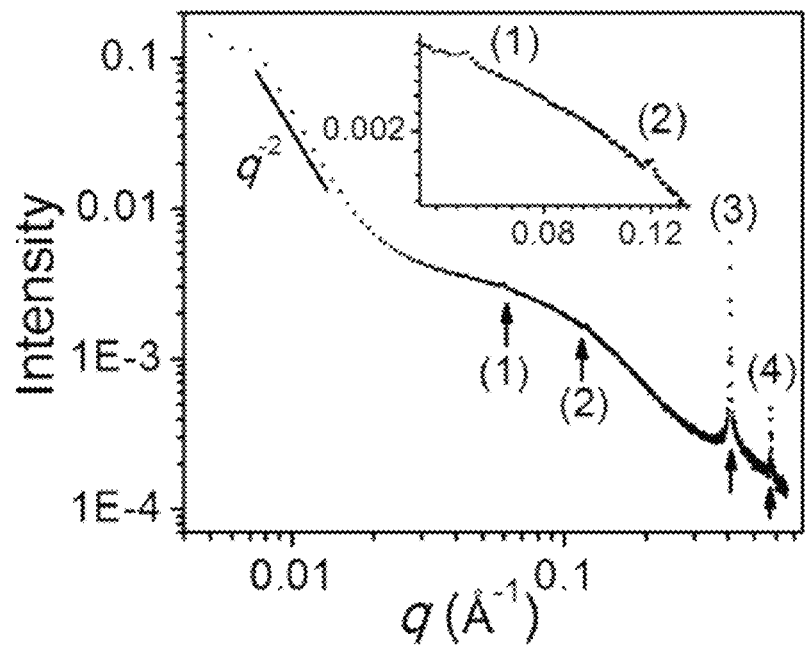
FIG. 4A shows a synchrotron SAXS scattering profile for solutions of NSI sheets showing q-2 dependence in the Porod region and diffraction peaks. Peaks (d-spacing): (1), 105 Å; (2), 52.4 Å; (3), 15.5 Å; and (4), 11.0 Å. Inset: expansion of the scattering profile corresponding to peaks (1) and (2).

The thicker assemblies derived from peptide NSI proved more physically robust to structural analysis and were studied in further detail. Synchrotron SAXS/WAXS data were collected on aqueous solutions of NSI in MOPS buffer. The resultant plot of intensity versus momentum transfer (q) displayed a complex dependence in which form factor scattering was convoluted with sharp Bragg reflections (FIG. 4A). The scattering intensity in the Porod region followed a power law dependence of the momentum transfer (q-2). The mass fractal dimension confirmed the sheet-like structure in solution. However, the dispersion in sheet thickness prevented extraction of the single-layer sheet height using Guinier analysis.

In the higher q region, four diffractions signals were observed; two peaks of relatively weak intensity at q values of 0.0600 Å-1 and 0.120 Å-1, and two strong, sharp peaks at q values of 0.405 Å-1 and 0.573 Å-1. The former signals correspond to d-spacings of 105 Å and 52.4 Å. The larger distance of 10.5 nm was consistent with the height of a single layer of laterally aligned collagen triple helices derived from NSI. The smaller spacing of 52.4 Å was approximately half that of the 105 Å spacing, which suggested that the larger distance corresponds to that of a (001) lattice plane while the smaller one is consistent with the (002) plane. The observation of a diffraction peak associated with the (002) plane suggests that the triple helices within a layer may be packed with an anti-parallel orientation between nearest neighbors. The weak intensity of these two reflections is indicative of the limited layer stacking in the z-direction, i.e., perpendicular to the surface of the two-dimensional sheet. The more intense signals at larger q values correspond to d-spacings of 15.5 Å, and 11.0 Å, which fall into the regime of reported inter-triple helical distances for quasi-hexagonal collagen packing Interestingly, these two d-spacings are related in that the 15.5 Å distance is equal to $\sqrt{2}$ times the 11.0 Å distance, which suggests that a two-dimensional square lattice may underlie the layered packing of collagen triple helices in nanosheets of NSI.

Figure 4B:
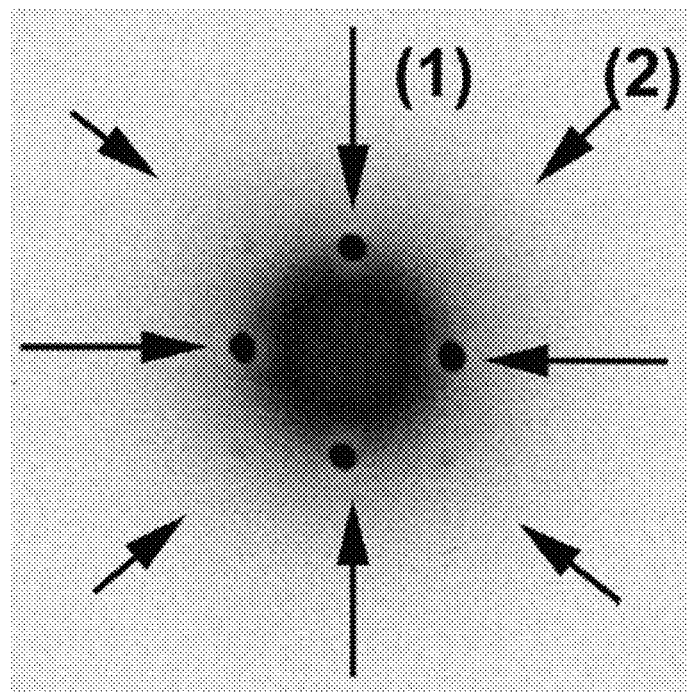
FIG. 4B shows electron diffraction pattern from NSI sheets. Diffraction spots were observed at 15.2 Å (1) and 10.8 Å (2)
Figure 4C:
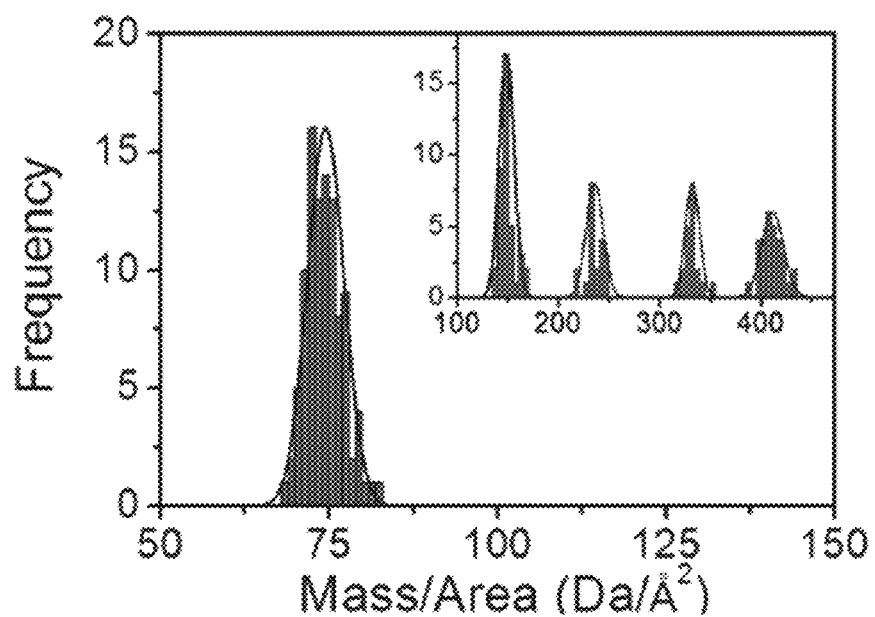
FIG. 4C shows data for mass per area measurements for NSI nanosheets in the single-layer and multi-layer (inset) regions.
Figure 4D:
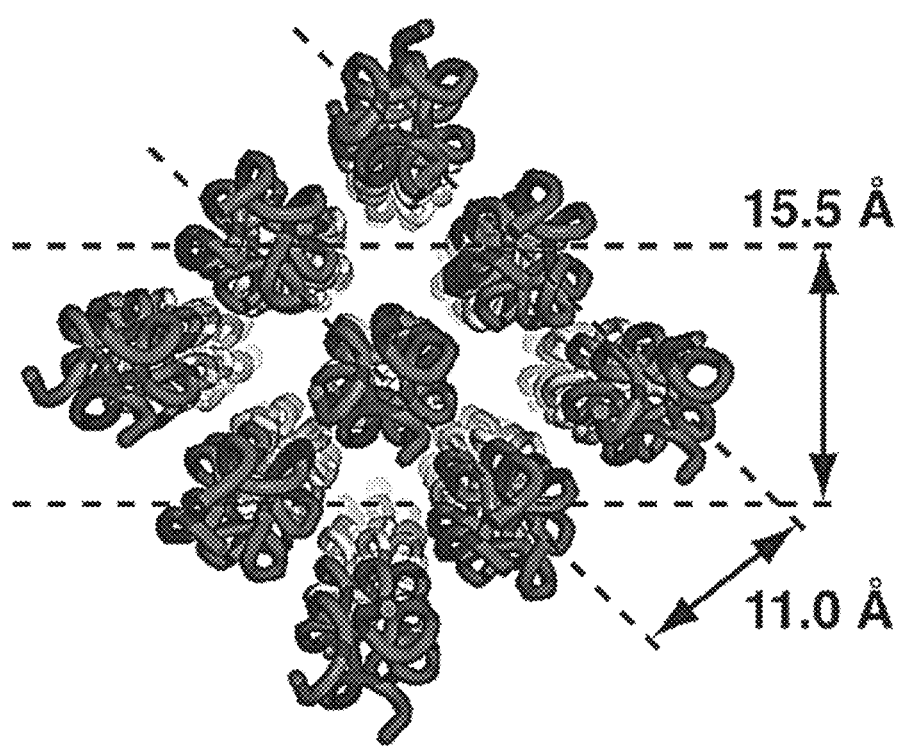
FIG. 4D illustrates a structural model of the 2D lattice of NSI sheets in a face-centered tetragonal arrangement of anti-parallel triple helices.

Electron diffraction (ED) data (FIG. 4B) from nanosheets of NSI provide additional support for a 2D-lattice of perpendicularly oriented, anti-parallel collagen triple helices. Sharp diffraction spots are observed at d-spacings of 15.2 Å and 10.8 Å, which are nearly identical to those observed in the solution SAXS measurements. Four-fold rotational symmetry was observed for the major and minor diffraction lattices, with a 45° angular offset between the two lattices. Lattice orientations for the larger d-spacing coincided with the directions of the sheet edges in the corresponding TEM image. In addition, scanning transmission electron microscopy (STEM) was employed to measure the mass-per-area (M/A) of freeze-dried specimens of NSI nanosheets. Single-layer sheets of NSI were observed to have an average mass-per-area value of 75 Da/Å2 (FIG. 4C). A theoretical mass-per-area of 84 Da/Å2 was calculated for a 15.5 Å×15.5 Å square unit cell containing two triples helices with individual masses of 10,044 Da from the NSI peptide (FIG. 4D), which compares well to the experimental value. Moreover, multi-layer sheets of NSI displayed a progression of M/A values between layers that differed by increments of approximately 80 Da/Å2 (FIG. 4C). This observation further substantiated a packing arrangement in which collagen layers were successively laminated to form the thick nanosheets derived from self-assembly of NSI.

Interactions with Substrates with Complementarily Functionalization

The well-ordered peptide packing within the nanosheets suggests that the surfaces of the assemblies should be decorated with functional groups derived from the termini of the peptide. The functional groups at the sheet surface should be accessible for interaction with exogenous substrates. As a test of this hypothesis, nanosheets derived from NSII were probed with cationic gold nanoparticles (10 nm core diameter functionalized with (11-mercaptoundecyl)-N,N,N-trimethylammonium bromide). The NSII sheets were chosen as substrates based on their greater chemical and thermodynamic stability due to the increased peptide length vis-à-vis sheets derived from NSI. The positively charge ammonium ions immobilized on the gold nanoparticles should interact selectively with the negatively charged C-terminal carboxylate groups of the peptides.

TEM and AFM analysis provide evidence for relatively dense packing of the nanoparticles at the surface of NSII nanosheets (FIGS. 5 A-B). The diameter of the nanoparticles is much larger than the distance between adjacent triple helices in the structure (circa 11 Å). The nanoparticles tend to spread out more or less evenly on the surface at lateral spacings that are larger still. Fourier transforms of the images do not provide evidence for an ordered arrangement of nanoparticles on the surface, which may indicate that either that the system has not achieved equilibrium under the experimental conditions or that the surface functional groups may be adopt a more disordered arrangement than the internal structure of the assembly.

Figure 5A:
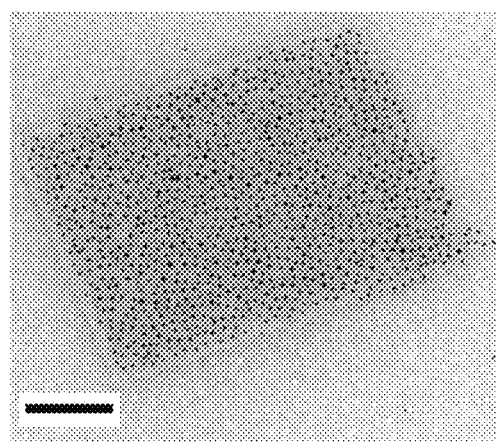
FIG. 5A shows TEM image of NSII nanosheet probed with cationic gold nanoparticles (scale bar=200 nm).
Figure 5B:
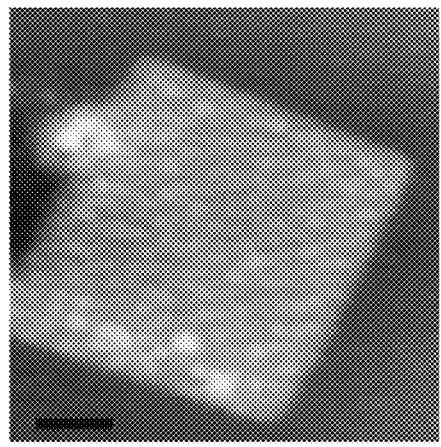
FIG. 5B shows AFM image of NSII nanosheet probed with cationic gold nanoparticles (scale bar=400 nm).
Figure 5C:
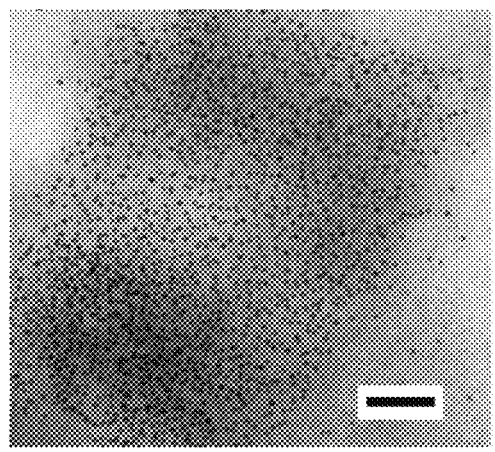
FIG. 5C shows TEM of NSII* nanosheets probed with streptavidin-tagged gold nanoparticles (scale bar=100 nm).

In order to promote a more specific interaction between the gold nanoparticles and nanosheets, a variant of peptide NSII, NSII*, was synthesized in which the N-terminus was capped with the D-biotin-15-amido-4,7,10,13-tetraoxapentadecyl group (biotin-dPEG$_4$). CD spectropolarimetry of peptide NSII* (2.8 mg/mL) in MOPS buffer (20 mM, pH 7.0) indicates the presence of the triple helical conformation of collagen, although the RPN value of 0.083 and Tm value of 54° C. suggest that the structure is less stable than that of NSII. NSII* self-assembles into nanosheets of similar morphology to NSII assemblies under identical conditions. Nanosheets derived from NSII* bind selectively to streptavidin-tagged gold nanoparticles (10 nm core-diameter) with high affinity (FIG. 5C). In contrast, nanosheets of NSII show no tendency to bind streptavidin tagged gold nanoparticles. The nanoparticle binding appears more dense and less uniform than the corresponding interaction of the NSII nanosheets with cationic gold nanoparticles (FIGS. 5A-B). The strength of the biotin-streptavidin interaction dictates that the binding of the nanoparticles is kinetically irreversible in the former case, which explains the differences in particle distribution at the sheet surface.

Figure 5D:
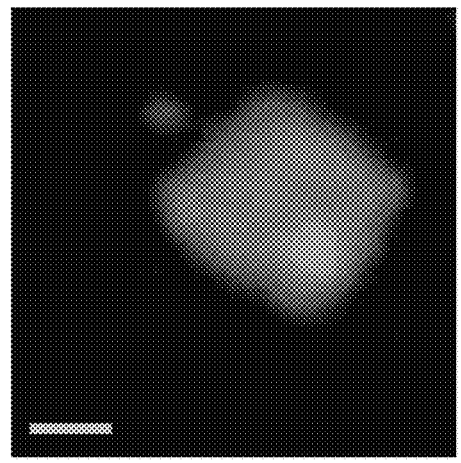
FIG. 5D shows Fluorescence microscopy image of a NSII* nanosheets immobilized on a biotinylated glass surface and stained with streptavidin-Alexa488 (scale bar=2 μm).

The biotin-streptavidin interaction could also be employed to selectively immobilize nanosheets of NSII* on functionalized surfaces (FIG. 5D). Biotin-derivatized glass surfaces were treated with excess streptavidin, followed by incubation with pre-assembled nanosheets of NSII*. The immobilized nanosheets were visualized using fluorescence microscopy after treatment with a solution of streptavidin-tagged Alexa488 dye. Reflection interference contrast microscopic (RICM) indicated that the fluorescent signal co-localized with the nanosheet. In general, the biotin capped nanosheets of NSII* could be immobilized on the surface with retention of the 2D shape. However, structural remodeling was also noted for some nanosheets upon immobilization, perhaps due to the strength of the biotin-streptavidin interaction. Although the NSII* nanosheets attached with random orientations to the functionalized surface, these data demonstrate the potential for construction of hybrid nanostructures through programmable non-covalent interactions for articulation of the nanosheets into functionally complex 2D-nanoarchitectonic platforms.

NSIII Containing (2S,4S)-4-Aminoproline (Amp)

NSIII self-assembles into nanosheets that display homogeneity in both lateral sheet dimension and thickness. (2S,4S)-4-aminoproline (amp). The sequence of peptide NSIII differs from the corresponding sequence of NSI in that the epimeric non-canonical imino acid (2S,4S)-4-aminoproline (amp) was employed in place of (2S,4R)-4-aminoproline (Amp) as the positively charged residue (FIGS. 6A-B). These two imino acids display preferences for opposite ring puckers, Cγ-endo and Cγ-exo, respectively, of the pyrrolidine side-chain.

Crystallographic analyses of collagen model peptides have indicated that the most common conformation for imino acid residues at the Xaa and Yaa positions are the Cγ-endo ring pucker and the Cγ-exo ring pucker, respectively. Therefore, the amp residue in the sequence of NSIII was encoded within the Xaa positions of the respective triad sequences. To compensate, the glutamic acid (Glu) residues were moved to Yaa positions of NSIII. The tri-block architecture of peptide NSI sequence was strictly maintained in NSIII such that direct structural comparisons could be made between these two peptide systems. Peptide NSIII was synthesized using microwave-assisted solidphase peptide synthesis and purified via preparative HPLC.

TEM image analysis (FIGS. 7A and 7B) demonstrated that peptide NSIII (4 mg/mL) self-assembles into nanosheets at 4° C. from MOPS buffer (20 mM, pH 7.0); conditions that are similar to those employed for self-assembly of nanosheets from peptide NSI. However, in contrast to the assemblies observed previously for the NSI, a homogeneous population nanosheets was observed for NSIII. Measurements of the diagonal length across the nanosheet surface indicated a narrow range of values for the NSIII assemblies (mean distance=679±57 nm), which was interpreted as an indication of the homogeneity of the assemblies. In comparison, a very broad distribution of sheet diagonal values (1-15 μm) was measured for the corresponding NSI nanosheets.

AFM analysis was employed to estimate the height of nanosheets of NSIII. A thickness of 9.6±0.4 nm was observed for the NSIII nanosheets (FIGS. 7C and 7D), which compared well to the value of 8.8±0.8 nm measured for single-layer nanosheets of NSI. A theoretical sheet thickness of 10.3 nm (36 residues×0.286 nm rise/residue for collagen triple helices) was calculated for single-layer nanosheets of NSI and NSIII, which correlates well with the height values measured from tapping mode AFM imaging under dry conditions. The AFM data support a structure for the NSIII nanosheets in which collagen triple helices pack into a single layer without stacking in the z-direction. In contrast, single-layer nanosheets of NSI are relatively rare. A wide dispersion of height values (10-250 nm) is observed from AFM measurements on the NSI nanosheets. These results suggested that multi-layer nanosheets are the norm for NSI, while all of the observed NSIII nanosheets corresponded to single layers of collagen triple helices.

Anti-Parallel Packing

Figure 8B:
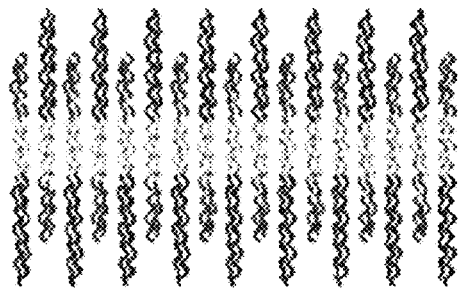
FIG. 8B illustrates a stacking layer of NS+.
Figure 8C:
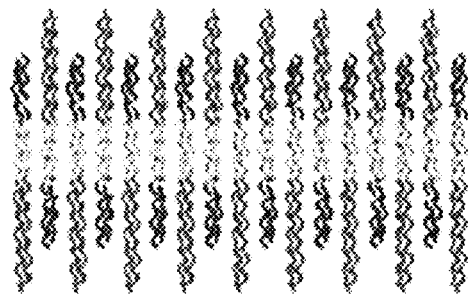
FIG. 8C illustrates a stacking layer of NS−.
Figure 8D:
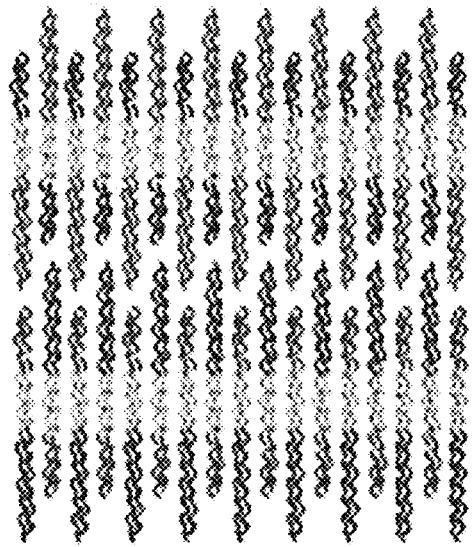
FIG. 8D illustrates stacking a layer of NS− on NS+.

Two asymmetric sequences NS+, and NS− were designed, using arginine at Yaa positions, and glutamate at Xaa positions for positively and negatively charged residue respectively. The positively charged triads of peptide NS+, and the negatively charged ones of peptide NS− were extended to seven repeats from original four repeats (FIG. 8A). It was believed that under such small sequence modification, both NS+ and NS− sequences would still adopt a similar anti-parallel packing mechanism as NSI. And the integrated three extra triple helices would stand out on sheet surfaces with an ordered geometry, like the "studs" on Lego® plates (FIGS. 8B and C). Coulombic interactions between the oppositely charged "studs" located on the surfaces of NS+ and NS− assemblies facilitate ordered nanosheet stacking. And adding more peptides compared to the other one, sandwiched structures might be constructed.

Circular dichroism (CD) was employed to assess the formation, and thermal stability of triple helix structures. NS+ and NS− peptides (1 mg/mL) in MES buffer (20 mM, pH 6.0) displayed a classic CD signature of collagen-like triple helix, with a maximum absorption from 222 to 224 nm, and a minimum absorption from 195 to 199 nm. Melting temperature of peptide NS+ (76° C.) was observed to be higher than the temperature of NS− (56° C.). NS+ and NS− shown higher thermal stability than NSI (32° C.), and NSIII (28° C.).

Transmission electron microscopy (TEM) was employed to investigate morphology of NS+, NS− assemblies (FIGS. 9A and B). NS+ exclusively self-associated into nanosheets over a period of hours, at concentrations down to 0.2 mg/mL from MES buffer (20 mM, pH 6.0), but the peptide NS− assemblies took over half year to develop detectable nanosheets, at concentrations higher than 5 mg/mL from MES buffer (20 mM, pH 6.0). Adding calcium cation as a potent glutamate binding ion, was found to efficiently reduce the association rate from months to hours. A NS variant peptide, NS-D, which comprises three (Asp-Hyp-Gly) triads was synthesized as the extended triads instead (Asp-Hyp-Gly)$_m$(Pro-Hyp-Gly)$_n$(Glu-Hyp-Gly)$_p$ (SEQ ID NO: 9) wherein m is 7, n is 4, and p is 4. NS-D peptides self-assembled into nanosheets within hours.

Tapping-mode atomic force microscope (AFM) was employed to estimate the thickness of nanosheets from NS+ and NSI− under dry conditions (FIG. 9A). Statistic analysis of height measurements indicated an average height of 9.4±1.0 nm for NS+ nanosheets, and 9.9±1.2 nm for NS nanosheets in the presence of calcium nitrate. The theoretical monolayer thicknesses were calculated to be 15 nm including two extra three triads (54 residues×0.286 nm rise/residue for collagen triple helices), and 10 nm excluding triads (36 residues×0.286 nm rise/residue). The later value correlated well with the thicknesses measured from AFM. The thickness values of NS+ and NS− nanosheets supported the mechanism of perpendicular packing between triple helices, and also approved the design that charged surfaces would prevented sheet stacking in z direction.

Figure 9C:
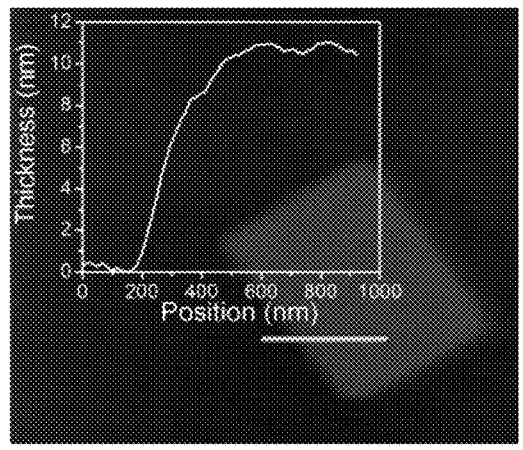
FIG. 9C shows data using atomic force microscope (AFM) indicating that as the NS−/NS+ ratio arise to be more than two, the nanosheet layer on surfaces of base would keep growing until reaching the lateral limits of base sheets.
Figure 9C:
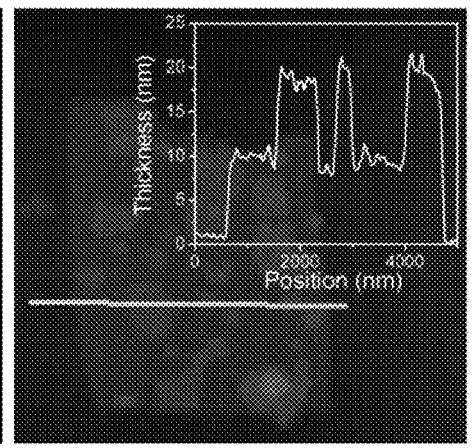
Figure 9C:
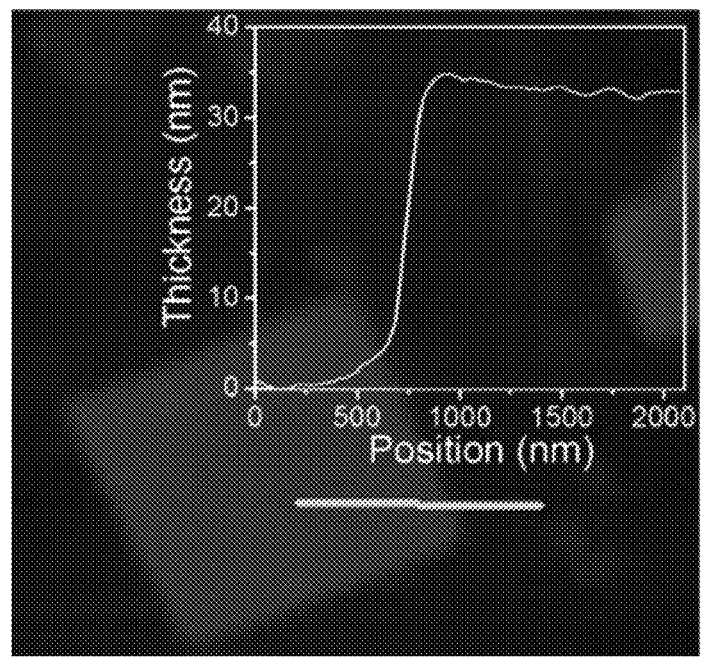

The morphology of structures from NS+ and NS− mixing were then investigated. Various layered structures were observed after adding NS− peptide solutions to the pre-formed NS+ sheet samples at different mixing ratios. With the concentration ratio of NS−/NS+ less than two, layered structures appeared as small sheets staying on surfaces of large base nanosheets (FIG. 9B). The thickness of surface and base nanosheets were measured to be about 10 nm, correlating with the calculated monolayer thickness at 10 nm. As the NS−/NS+ ratio arise to be more than two, the nanosheet layer on surfaces of base would keep growing until reaching the lateral limits of base sheets (FIG. 9C). AFM assay indicated an average height of 34±2.0 nm for the final mature structures, in agreement with the theoretical height at 36 nm for a sandwiched structure, without considering the extra triads on two surfaces (126 residues×0.286 nm rise/residue for collagen triple helices).

On the two surfaces of NS+ sheets, NS− peptides are enable to assemble and grow into complete layers, resulting in a sandwiched structure. The requirement of twice the concentrations of NS− as NS+ coincided with the fact that there is no difference between two faces of NS+ sheets in attracting and promoting NS layer formations.

What is claimed:

1. A polypeptide comprising
   a) an first terminal segment comprising a three amino acid repeat starting with two amino acids, wherein one of the two amino acids is proline substituted with an amino group, and ending with a glycine;
   b) a middle segment comprising a three amino acid repeat starting with two amino acids, wherein one of the two amino acids comprises a side chain with an hydroxy group, and ending with a glycine;
   c) a second terminal segment comprising a three amino acid repeat starting with two amino acids, wherein one of the two amino acids comprises side chain with a carboxylic acid group, and ending with a glycine.

2. The polypeptide of claim 1, wherein the first terminal segment comprises a three amino acid repeat starting with two amino acids, wherein one of the two amino acids is a hydrophobic amino acid, wherein one of the two amino acids is proline substituted with an amino group, and ending with a glycine.

3. The polypeptide of claim 1, wherein the middle segment comprises a three amino acid repeat starting with two amino acids, wherein one of the two amino acids is a hydrophobic amino acid, wherein one of the two amino acids comprises a side chain with an hydroxy group, and ending with a glycine.

4. The polypeptide of claim 1, wherein the second terminal segment comprises a three amino acid repeat starting with two amino acids, wherein one of the two amino acids comprises side chain with a carboxylic acid group, wherein one of the two amino acids comprises a side chain with a hydroxy group, and ending with a glycine.

5. The polypeptide of claim 1, wherein the hydrophobic amino acid is proline.

6. The polypeptide of claim 1, wherein one of the two amino acids comprising a side chain with a hydroxy group is proline substituted with a hydroxy group.

7. The polypeptide of claim 1, wherein the first terminal segment is the N-terminal segment and the second terminal segment is the C-terminal segment.

8. The polypeptide of claim 1, wherein the first terminal segment is the N-terminal segment and the N-terminal amino acid is (2S,4S)-4-aminoproline.

9. A composition comprising a polypeptide comprising the sequence $(X^1—Y^1\text{-Gly})_m\text{-}(X^2—Y^2\text{-Gly})_n\text{-}(X^3—Y^3\text{-Gly})_p$ wherein, $X^1$ is any amino acid, $Y^1$ is any amino acid, m is three or more,
provided that proline is the most common $X^1$,
provided that proline substituted with an amino group is the most common $Y^1$;

$X^2$ is any amino acid, $Y^2$ is any amino acid, n is three or more,
provided that proline is the most common $X^2$,
provided that proline substituted with an hydroxy group is the most common $Y^2$;

$X^3$ is any amino acid, $Y^3$ is any amino acid, p is three or more,
provided that an amino acid comprises side chain with a carboxylic acid group is the most common $X^3$,
provided that proline substituted with an hydroxy group is the most common $Y^3$.

10. The composition of claim 9, wherein $X^1$ is proline and $Y^1$ is aminoproline.

11. The composition of claim 9, wherein $X^2$ is proline and $Y^2$ is hydoxyproline.

12. The composition of claim 9, wherein $X^3$ is Glu or Asp and $Y^3$ is hydroxyproline.

13. A composition comprising a polypeptide comprising the sequence $(X^1—Y^1\text{-Gly})_m\text{-}(X^2—Y^2\text{-Gly})_n\text{-}(X^3—Y^3\text{-Gly})_p$ wherein, $X^1$ is any amino acid, $Y^1$ is any amino acid, m is three or more,
provided that that proline substituted with an amino group is the most common $X^1$,
provided that proline substituted with an hydroxy group is the most common $Y^1$;

$X^2$ is any amino acid, $Y^2$ is any amino acid, n is three or more,
provided that proline is the most common $X^2$,
provided that proline substituted with an hydroxy group is the most common $Y^2$;

$X^3$ is any amino acid, $Y^3$ is any amino acid, p is three or more,
provided that proline is the most common $X^3$,
provided that an amino acid comprises side chain with a carboxylic acid group is the most common $Y^3$.

14. The composition of claim 13, wherein $X^1$ is (2S,4S)-4-aminoproline.

15. The composition of claim 13, wherein $X^1$ is (2S,4S)-4-aminoproline and $Y^1$ is hydroxyproline.

16. The composition of claim 13, wherein $X^2$ is proline and $Y^2$ is hydoxyproline.

17. The composition of claim 13, wherein $X^3$ is proline and $Y^3$ is Glu or Asp.

18. A two-dimensional material comprising a polypeptide of claim 13.

19. A material comprising 1) a first layer of first polypeptide fibers comprising a) an first terminal segment comprising a three amino acid repeat starting with two amino acids, wherein one of the two amino acids is an amino acid comprising a side chain substituted with an amino group, and ending with a glycine; b) a middle segment comprising a three amino acid repeat starting with two amino acids, wherein one of the two amino acids comprises a side chain with an hydroxy group, and ending with a glycine; c) a second terminal segment comprising a three amino acid repeat starting with two amino acids, wherein one of the two amino acids comprises side chain with a carboxylic acid group, and ending with a glycine;

2) a second layer comprising polypeptide fibers comprising a) an first terminal segment comprising a three amino acid repeat starting with two amino acids, wherein one of the two amino acids is an amino acid comprising a side chain substituted with an amino group, and ending with a glycine; b) a middle segment comprising a three amino acid repeat starting with two amino acids, wherein one of the two amino acids comprises a side chain with an hydroxy group, and ending with a glycine; c) a second terminal segment comprising a three amino acid repeat starting with two amino acids, wherein one of the two amino acids comprises a side chain with a carboxylic acid group, and ending with a glycine.

20. The material of claim 19, wherein the first terminal segment of the first polypeptide fibers has one or more extra three amino acid repeats than the first terminal segment of the second polypeptide fibers and the first polypeptide fibers and the second polypeptide fibers are of the same length.

* * * * *